US011229751B2

(12) United States Patent
Desborough et al.

(10) Patent No.: US 11,229,751 B2
(45) Date of Patent: *Jan. 25, 2022

(54) PERSONALIZING PRESET MEAL SIZES IN INSULIN DELIVERY SYSTEM

(71) Applicant: Bigfoot Biomedical, Inc., Milpitas, CA (US)

(72) Inventors: Lane Desborough, Milpitas, CA (US); Bryan Mazlish, Milpitas, CA (US); Andrew Bochenko, San Jose, CA (US); Ross Naylor, Fullerton, CA (US); Jeff Boissier, San Jose, CA (US); Sabine Kabel-Eckes, Mountain View, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/717,845

(22) Filed: Sep. 27, 2017

(65) Prior Publication Data

US 2018/0089395 A1    Mar. 29, 2018

Related U.S. Application Data

(60) Provisional application No. 62/400,366, filed on Sep. 27, 2016.

(51) Int. Cl.
*A61M 5/172* (2006.01)
*A61M 5/32* (2006.01)
(Continued)

(52) U.S. Cl.
CPC ........ *A61M 5/3202* (2013.01); *A61M 5/1723* (2013.01); *G06F 3/0482* (2013.01);
(Continued)

(58) Field of Classification Search
CPC .............. A61M 5/1723; A61M 5/5202; A61M 5/3202; A61M 2205/505;
(Continued)

(56) References Cited

U.S. PATENT DOCUMENTS 2,605,765 A    8/1952  Kollsman
3,886,938 A    6/1975  Szabo et al.
(Continued)

FOREIGN PATENT DOCUMENTS

CA       2543545 A1     5/2005
CN     101610718 A    12/2009
(Continued)

OTHER PUBLICATIONS

Sindaco et al., Use of the Short-acting Insulin Analogue Lispro in Intensive Treatment of Type 1 Diabetes Mellitus: Importance of Appropriate Replacement of Basal Insulin and Time-interval Injection-meal, Diabetic Medicine 1998, pp. 592-600. (Year: 1998).*
(Continued)

*Primary Examiner* — Sanchita Roy
(74) *Attorney, Agent, or Firm* — TraskBritt

(57) ABSTRACT

A method may include displaying at least three icons on a user interface of a mobile device, including a first icon associated with the at least three icons associated with a first carbohydrate level, a second icon associated with the at least three icons associated with a second carbohydrate level, and a third icon associated with the at least three icons associated with a third carbohydrate level. The method may also include receiving a user selection of one of the three icons through the user interface of the mobile device, and determining an insulin bolus level from the user selection. The method may also include communicating the insulin bolus level to an insulin delivery device.

16 Claims, 8 Drawing Sheets

(51) Int. Cl.
*G16H 20/17* (2018.01)
*G16H 50/20* (2018.01)
*G16H 20/10* (2018.01)
*G06F 3/0481* (2013.01)
*G06F 3/0482* (2013.01)
*G06F 3/0484* (2013.01)
*G16H 10/60* (2018.01)
*G16H 40/63* (2018.01)
*G06F 3/0488* (2013.01)

(52) U.S. Cl.
CPC ...... *G06F 3/04817* (2013.01); *G06F 3/04847* (2013.01); *G16H 20/10* (2018.01); *G16H 20/17* (2018.01); *G16H 50/20* (2018.01); *A61M 2205/3303* (2013.01); *A61M 2205/3306* (2013.01); *A61M 2205/3561* (2013.01); *A61M 2205/50* (2013.01); *A61M 2205/505* (2013.01); *A61M 2205/52* (2013.01); *A61M 2230/201* (2013.01); *G06F 3/04883* (2013.01); *G16H 10/60* (2018.01); *G16H 40/63* (2018.01)

(58) Field of Classification Search
CPC .. A61M 2205/3303; A61M 2205/3306; A61M 2205/50; A61M 2205/52; A61M 2230/20; G16H 50/20; G16H 20/10; G16H 20/17; G16H 50/30; G16H 10/60; G16H 40/60; G16H 40/63; G16H 20/60; G06F 3/04817; G06F 3/0482; G06F 3/04847; G06F 3/193468; G06F 19/3468; G06F 3/048; G06F 3/048
USPC .......................................................... 715/771
See application file for complete search history.

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | Decant et al. |
| 4,493,704 A | 1/1985 | Beard et al. |
| 4,529,401 A | 7/1985 | Leslie et al. |
| 4,681,569 A | 7/1987 | Coble et al. |
| 4,749,109 A | 6/1988 | Kamen |
| 4,838,857 A | 6/1989 | Strowe et al. |
| 4,850,817 A | 7/1989 | Nason et al. |
| 5,045,064 A | 9/1991 | Idriss |
| 5,088,981 A | 2/1992 | Howson et al. |
| 5,088,990 A | 2/1992 | Hivale et al. |
| D325,781 S | 4/1992 | Moller-Jensen |
| 5,190,522 A | 3/1993 | Wojcicki et al. |
| 5,225,763 A | 7/1993 | Krohn et al. |
| 5,250,027 A | 10/1993 | Lewis et al. |
| 5,261,882 A | 11/1993 | Sealfon |
| 5,314,412 A | 5/1994 | Rex |
| 5,335,994 A | 8/1994 | Weynant |
| 5,338,157 A | 8/1994 | Blomquist |
| 5,342,180 A | 8/1994 | Daoud |
| D351,469 S | 10/1994 | Okamoto |
| 5,389,078 A | 2/1995 | Zalesky et al. |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,554,123 A | 9/1996 | Herskowitz |
| 5,569,186 A | 10/1996 | Lord et al. |
| 5,626,566 A | 5/1997 | Petersen et al. |
| 5,637,095 A | 6/1997 | Nason et al. |
| 5,640,954 A | 6/1997 | Pfeiffer et al. |
| 5,665,065 A | 9/1997 | Colman et al. |
| 5,678,571 A | 10/1997 | Brown |
| 5,718,562 A | 2/1998 | Lawless et al. |
| D393,264 S | 4/1998 | Leung |
| 5,741,216 A | 4/1998 | Hemmingsen et al. |
| 5,766,155 A | 6/1998 | Hyman et al. |
| 5,772,635 A | 6/1998 | Dastur et al. |
| 5,816,306 A | 10/1998 | Giacomel |
| 5,852,803 A | 12/1998 | Ashby et al. |
| 5,858,001 A | 1/1999 | Tsals et al. |
| 5,918,603 A | 7/1999 | Brown |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,032,119 A | 2/2000 | Brown et al. |
| 6,033,377 A | 3/2000 | Rasmussen et al. |
| 6,045,537 A | 4/2000 | Klitmose |
| D424,036 S | 5/2000 | Arora et al. |
| 6,056,728 A | 5/2000 | Von Schuckmann |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,354,996 B1 | 3/2002 | Drinan et al. |
| 6,368,314 B1 | 4/2002 | Kipfer et al. |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| D460,053 S | 7/2002 | Choi |
| 6,427,088 B1 | 7/2002 | Bowman et al. |
| D461,241 S | 8/2002 | Moberg et al. |
| D461,891 S | 8/2002 | Moberg |
| 6,436,072 B1 | 8/2002 | Kullas et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,605,067 B1 | 8/2003 | Larsen |
| 6,613,019 B2 | 9/2003 | Munk |
| 6,641,533 B2 | 11/2003 | Causey et al. |
| 6,648,821 B2 | 11/2003 | Lebel et al. |

(56) References Cited

U.S. PATENT DOCUMENTS

| | | |
|---|---|---|
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Moeller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman et al. |
| 6,956,572 B2 | 10/2005 | Zaleski |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,096,431 B2 | 8/2006 | Tambata et al. |
| 7,104,972 B2 | 9/2006 | Moller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,232,423 B2 | 6/2007 | Mernoee |
| D545,837 S | 7/2007 | Haldimann et al. |
| 7,241,265 B2 | 7/2007 | Cummings et al. |
| D550,227 S | 9/2007 | Sato et al. |
| D553,625 S | 10/2007 | Burns et al. |
| D554,140 S | 10/2007 | Armendariz |
| 7,291,107 B2 | 11/2007 | Hellwig et al. |
| 7,343,197 B2 | 3/2008 | Shusterman |
| 7,454,359 B2 | 11/2008 | Rosenfeld et al. |
| 7,479,949 B2 | 1/2009 | Jobs et al. |
| D592,223 S | 5/2009 | Neuhaus |
| 7,534,226 B2 | 5/2009 | Mernoe et al. |
| 7,553,281 B2 | 6/2009 | Hellwig et al. |
| 7,555,727 B2 | 6/2009 | Hawkins et al. |
| 7,570,980 B2 | 8/2009 | Ginsberg |
| D600,341 S | 9/2009 | Loerwald |
| D603,421 S | 11/2009 | Ebeling et al. |
| D607,099 S | 12/2009 | Loerwald |
| 7,647,237 B2 | 1/2010 | Malave et al. |
| D614,587 S | 4/2010 | Yodfat et al. |
| 7,695,434 B2 | 4/2010 | Malecha |
| 7,708,717 B2 | 5/2010 | Estes et al. |
| 7,717,903 B2 | 5/2010 | Estes et al. |
| 7,751,907 B2 | 7/2010 | Blomquist |
| D623,753 S | 9/2010 | Saffer et al. |
| 7,789,859 B2 | 9/2010 | Estes et al. |
| 7,828,528 B2 | 11/2010 | Estes et al. |
| 7,837,647 B2 | 11/2010 | Estes et al. |
| 7,850,641 B2 | 12/2010 | Lebel et al. |
| 7,871,376 B2 | 1/2011 | Brown |
| D632,699 S | 2/2011 | Judy et al. |
| 7,878,975 B2 | 2/2011 | Liljeryd et al. |
| 7,887,512 B2 | 2/2011 | Estes et al. |
| 7,931,613 B2 | 4/2011 | Haueter et al. |
| 7,938,797 B2 | 5/2011 | Estes |
| D640,269 S | 6/2011 | Chen |
| 7,956,845 B2 | 6/2011 | Lee |
| D642,191 S | 7/2011 | Barnett et al. |
| 8,012,119 B2 | 9/2011 | Estes et al. |
| D648,804 S | 11/2011 | Coulter |
| D652,426 S | 1/2012 | Anzures |
| 8,132,101 B2 | 3/2012 | Buck et al. |
| D656,950 S | 4/2012 | Shallcross et al. |
| 8,156,070 B2 | 4/2012 | Buck et al. |
| D660,315 S | 5/2012 | Anzures |
| D661,701 S | 6/2012 | Brown et al. |
| 8,202,249 B2 | 6/2012 | Iio et al. |
| 8,217,946 B2 | 7/2012 | Halpern et al. |
| 8,219,222 B2 | 7/2012 | Blomquist |
| 8,221,345 B2 | 7/2012 | Blomquist |
| 8,221,359 B2 | 7/2012 | Kristensen et al. |
| 8,231,562 B2 | 7/2012 | Buck et al. |
| D665,409 S | 8/2012 | Gupta et al. |
| 8,237,715 B2 | 8/2012 | Buck et al. |
| 8,250,483 B2 | 8/2012 | Blomquist |
| 8,257,652 B2 | 9/2012 | Drucker et al. |
| 8,257,653 B2 | 9/2012 | Drucker et al. |
| 8,262,616 B2 | 9/2012 | Grant et al. |
| 8,273,296 B2 | 9/2012 | Drucker et al. |
| D669,165 S | 10/2012 | Estes et al. |
| D669,166 S | 10/2012 | Estes et al. |
| D669,167 S | 10/2012 | Estes et al. |
| 8,279,226 B2 | 10/2012 | Krieftewirth |
| 8,310,415 B2 | 11/2012 | McLaughlin et al. |
| 8,337,469 B2 | 12/2012 | Eberhart et al. |
| 8,357,091 B2 | 1/2013 | Say et al. |
| 8,365,065 B2 | 1/2013 | Gejdos et al. |
| 8,372,005 B2 | 2/2013 | Say et al. |
| D682,289 S | 5/2013 | Dijulio et al. |
| D682,304 S | 5/2013 | Mierau et al. |
| D682,305 S | 5/2013 | Mierau et al. |
| 8,439,834 B2 | 5/2013 | Schmelzeisen-Redeker et al. |
| D683,738 S | 6/2013 | Wujcik et al. |
| D687,062 S | 7/2013 | Gardner et al. |
| D687,541 S | 8/2013 | Estes et al. |
| 8,514,086 B2 | 8/2013 | Harper et al. |
| D689,087 S | 9/2013 | Fymat |
| D689,090 S | 9/2013 | Impas et al. |
| D689,523 S | 9/2013 | Galbraith et al. |

(56) References Cited

U.S. PATENT DOCUMENTS

| | | |
|---|---|---|
| D689,874 S | 9/2013 | Brinda et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| D691,258 S | 10/2013 | Estes et al. |
| D691,259 S | 10/2013 | Estes et al. |
| D693,114 S | 11/2013 | Lemanski, Sr. |
| D693,365 S | 11/2013 | Gardner et al. |
| 8,579,815 B2 | 11/2013 | Galley et al. |
| 8,601,005 B2 | 12/2013 | Bousamra et al. |
| 8,615,366 B2 | 12/2013 | Galley et al. |
| D697,204 S | 1/2014 | Maier et al. |
| 8,622,906 B2 | 1/2014 | Say et al. |
| D698,808 S | 2/2014 | Funabashi et al. |
| D699,741 S | 2/2014 | Wantland et al. |
| 8,657,779 B2 | 2/2014 | Blomquist |
| D701,879 S | 4/2014 | Foit et al. |
| D702,258 S | 4/2014 | Wantland et al. |
| D705,261 S | 5/2014 | Holz et al. |
| 8,719,945 B2 | 5/2014 | Birtwhistle et al. |
| 8,756,074 B2 | 6/2014 | Brzustowicz |
| 8,761,940 B2 | 6/2014 | Long et al. |
| D709,080 S | 7/2014 | Kim |
| D709,183 S | 7/2014 | Kemlein |
| 8,774,887 B2 | 7/2014 | Say et al. |
| 8,816,862 B2 | 8/2014 | Harper et al. |
| 8,839,106 B2 | 9/2014 | Lee et al. |
| D714,816 S | 10/2014 | Varon |
| D715,835 S | 10/2014 | Montgomery et al. |
| D716,340 S | 10/2014 | Bresin et al. |
| D717,822 S | 11/2014 | Brotman et al. |
| D717,823 S | 11/2014 | Brotman et al. |
| D717,830 S | 11/2014 | Brinda et al. |
| D718,438 S | 11/2014 | Davis et al. |
| 8,895,315 B2 | 11/2014 | Batman et al. |
| D719,186 S | 12/2014 | Kim |
| 8,929,823 B2 * | 1/2015 | Mears ............... A61B 5/14532 455/41.2 |
| 8,961,465 B2 | 2/2015 | Blomquist |
| D724,616 S | 3/2015 | Jou |
| 8,992,464 B2 * | 3/2015 | Bashan ............. A61B 5/14532 604/66 |
| D727,336 S | 4/2015 | Allison et al. |
| 9,008,803 B2 | 4/2015 | Blomquist |
| 9,022,996 B2 | 5/2015 | Eberhart et al. |
| 9,033,877 B2 | 5/2015 | Werner et al. |
| 9,041,730 B2 | 5/2015 | Johnson et al. |
| D730,929 S | 6/2015 | Yu et al. |
| D733,175 S | 6/2015 | Bae |
| D733,179 S | 6/2015 | Kwon |
| 9,050,409 B2 | 6/2015 | Haueter et al. |
| 9,056,165 B2 * | 6/2015 | Steil .................. A61M 5/1723 |
| 9,072,477 B2 | 7/2015 | Say et al. |
| 9,076,107 B2 | 7/2015 | Cameron et al. |
| D736,792 S | 8/2015 | Brinda et al. |
| D737,278 S | 8/2015 | Shin et al. |
| D738,907 S | 9/2015 | Cabrera-Cordon et al. |
| D738,913 S | 9/2015 | Cabrera-Cordon et al. |
| D738,914 S | 9/2015 | Torres et al. |
| 9,134,823 B2 | 9/2015 | Grant et al. |
| 9,136,939 B2 | 9/2015 | Galley et al. |
| D741,891 S | 10/2015 | Gardner et al. |
| 9,159,148 B2 | 10/2015 | Boyer et al. |
| 9,171,343 B1 | 10/2015 | Fischell et al. |
| D743,435 S | 11/2015 | Herold et al. |
| 9,186,113 B2 | 11/2015 | Harper et al. |
| D744,505 S | 12/2015 | Wilberding et al. |
| D745,050 S | 12/2015 | Kwon |
| D745,543 S | 12/2015 | Kim et al. |
| D746,314 S | 12/2015 | Jung et al. |
| 9,198,623 B2 | 12/2015 | Fern et al. |
| D746,848 S | 1/2016 | Bovet et al. |
| D748,646 S | 2/2016 | Kim et al. |
| D749,097 S | 2/2016 | Zou et al. |
| D751,081 S | 3/2016 | Kim et al. |
| D751,090 S | 3/2016 | Hu et al. |
| D751,585 S | 3/2016 | Kaufthal et al. |
| D751,586 S | 3/2016 | Kaufthal et al. |
| D752,604 S | 3/2016 | Zhang |
| D752,736 S | 3/2016 | Chandrasenan et al. |
| D753,139 S | 4/2016 | Bovet |
| D753,177 S | 4/2016 | Mierau et al. |
| D753,685 S | 4/2016 | Zimmerman et al. |
| D754,670 S | 4/2016 | Park |
| D754,685 S | 4/2016 | Carlton et al. |
| D754,689 S | 4/2016 | Lee |
| D754,713 S | 4/2016 | Zhang et al. |
| D754,714 S | 4/2016 | Zhang et al. |
| D755,206 S | 5/2016 | Lee et al. |
| D755,830 S | 5/2016 | Chaudhri et al. |
| D757,026 S | 5/2016 | Lim et al. |
| D757,047 S | 5/2016 | Cornwell et al. |
| D758,433 S | 6/2016 | Lee et al. |
| D760,752 S | 7/2016 | Anzures et al. |
| D761,843 S | 7/2016 | Kim |
| D762,234 S | 7/2016 | Li et al. |
| D762,675 S | 8/2016 | Lim et al. |
| D763,285 S | 8/2016 | Chan et al. |
| D763,860 S | 8/2016 | Sunshine et al. |
| D763,921 S | 8/2016 | Dharwada et al. |
| D765,092 S | 8/2016 | Chaudhri et al. |
| D765,710 S | 9/2016 | Anzures et al. |
| D766,257 S | 9/2016 | Zhang et al. |
| D766,424 S | 9/2016 | Anderson et al. |
| D768,144 S | 10/2016 | Kim et al. |
| D768,687 S | 10/2016 | Bae et al. |
| D769,314 S | 10/2016 | Piroddi et al. |
| D769,322 S | 10/2016 | Rajeswaran et al. |
| D769,325 S | 10/2016 | Casalegno et al. |
| D771,672 S | 11/2016 | Tanabe et al. |
| D772,924 S | 11/2016 | Begin et al. |
| D773,510 S | 12/2016 | Foss et al. |
| D776,137 S | 1/2017 | Chaudhri et al. |
| D776,253 S | 1/2017 | Li |
| D776,702 S | 1/2017 | Huang et al. |
| D777,906 S | 1/2017 | Anderson et al. |
| D781,305 S | 3/2017 | Lau |
| D781,908 S | 3/2017 | Bhandari et al. |
| D783,652 S | 4/2017 | Guan et al. |
| D784,372 S | 4/2017 | Kovchiy |
| D786,266 S | 5/2017 | Van et al. |
| D786,270 S | 5/2017 | Barry et al. |
| D788,138 S | 5/2017 | Lee et al. |
| D788,140 S | 5/2017 | Hemsley et al. |
| D788,145 S | 5/2017 | Sullivan et al. |
| D788,808 S | 6/2017 | Chaudhri et al. |
| D789,419 S | 6/2017 | Chaudhri et al. |
| D790,562 S | 6/2017 | Nageli et al. |
| D790,583 S | 6/2017 | Kay et al. |
| D791,806 S | 7/2017 | Brewington et al. |
| 9,707,336 B2 | 7/2017 | Dang et al. |
| D794,649 S | 8/2017 | Niijima et al. |
| D795,284 S | 8/2017 | Miller et al. |
| D795,294 S | 8/2017 | Faulkner et al. |
| 9,717,849 B2 | 8/2017 | Mhatre et al. |
| D797,771 S | 9/2017 | Caporal et al. |
| D797,772 S | 9/2017 | Mizono et al. |
| D798,318 S | 9/2017 | Ferguson et al. |
| D798,895 S | 10/2017 | Kim et al. |
| D800,757 S | 10/2017 | Mullen et al. |
| D801,519 S | 10/2017 | Sabin et al. |
| D801,990 S | 11/2017 | Reissner et al. |
| D802,607 S | 11/2017 | Apodaca et al. |
| D803,850 S | 11/2017 | Chang et al. |
| D804,505 S | 12/2017 | Hoffman et al. |
| D805,541 S | 12/2017 | Juliano |
| D806,748 S | 1/2018 | Van et al. |
| D806,749 S | 1/2018 | Van et al. |
| D806,750 S | 1/2018 | Van et al. |
| D808,417 S | 1/2018 | Mander et al. |
| D808,974 S | 1/2018 | Chiappone et al. |
| D809,134 S | 1/2018 | Crothall |
| 9,878,097 B2 | 1/2018 | Estes |
| D810,095 S | 2/2018 | Vali et al. |

(56) References Cited

U.S. PATENT DOCUMENTS

| | | |
|---|---|---|
| D812,072 S | 3/2018 | Hoffman |
| D815,665 S | 4/2018 | Li et al. |
| D816,093 S | 4/2018 | Mazur et al. |
| 9,931,454 B2 | 4/2018 | Lo et al. |
| D816,708 S | 5/2018 | Riedel et al. |
| D816,709 S | 5/2018 | Riedel et al. |
| D816,713 S | 5/2018 | Kang |
| D819,065 S | 5/2018 | Xie et al. |
| D819,067 S | 5/2018 | Behzadi et al. |
| D819,646 S | 6/2018 | Jow et al. |
| D820,304 S | 6/2018 | Coffman et al. |
| D821,437 S | 6/2018 | Chaudhri et al. |
| D828,375 S | 9/2018 | Mok et al. |
| D828,377 S | 9/2018 | Dhide |
| D830,385 S | 10/2018 | Lepine et al. |
| D835,658 S | 12/2018 | Chan et al. |
| D835,659 S | 12/2018 | Anzures et al. |
| D837,809 S | 1/2019 | Kagatsume et al. |
| D839,294 S | 1/2019 | Mazlish et al. |
| 10,263,802 B2 | 4/2019 | Burns et al. |
| D852,837 S | 7/2019 | Mazlish et al. |
| D857,724 S | 8/2019 | Clediere et al. |
| D858,566 S | 9/2019 | Bacchus |
| D858,567 S | 9/2019 | Bacchus |
| 10,410,538 B2 | 9/2019 | Simpson et al. |
| D863,343 S | 10/2019 | Mazlish et al. |
| 10,426,896 B2 | 10/2019 | Desborough et al. |
| D870,767 S | 12/2019 | Villafane |
| D875,111 S | 2/2020 | Clediere |
| D875,124 S | 2/2020 | Yan |
| 10,572,107 B1 | 2/2020 | Beebe et al. |
| D883,319 S | 5/2020 | Caro et al. |
| D884,716 S | 5/2020 | Tan et al. |
| D886,850 S | 6/2020 | Kim et al. |
| D888,748 S | 6/2020 | Valladares et al. |
| D890,206 S | 7/2020 | Felkins et al. |
| D905,091 S | 12/2020 | Henry et al. |
| 10,871,889 B2 | 12/2020 | Ballantyne et al. |
| 10,904,270 B2 | 1/2021 | Muddu et al. |
| 2001/0041869 A1 | 11/2001 | Causey et al. |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0175931 A1 | 11/2002 | Holtz et al. |
| 2002/0177810 A1 | 11/2002 | Reilly et al. |
| 2003/0028089 A1 | 2/2003 | Galley et al. |
| 2003/0055380 A1 | 3/2003 | Flaherty |
| 2003/0065308 A1 | 4/2003 | Lebel et al. |
| 2003/0088238 A1 | 5/2003 | Poulsen et al. |
| 2003/0167035 A1 | 9/2003 | Flaherty et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0093331 A1 | 5/2004 | Garner et al. |
| 2004/0116866 A1 | 6/2004 | Gorman et al. |
| 2004/0127844 A1 | 7/2004 | Flaherty |
| 2004/0153032 A1 | 8/2004 | Garibotto et al. |
| 2004/0153257 A1 | 8/2004 | Munk |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0038674 A1 | 2/2005 | Braig et al. |
| 2005/0044500 A1 | 2/2005 | Orimoto et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0114374 A1 | 5/2005 | Juszkiewicz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192494 A1 | 9/2005 | Ginsberg |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2006/0276771 A1* | 12/2006 | Galley ................. G16H 20/17 604/503 |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0171087 A1 | 7/2007 | Shimazu et al. |
| 2007/0179444 A1 | 8/2007 | Causey et al. |
| 2007/0213657 A1* | 9/2007 | Jennewine ........... A61B 5/0031 604/66 |
| 2007/0239116 A1 | 10/2007 | Follman et al. |
| 2008/0051716 A1 | 2/2008 | Stutz |
| 2008/0059158 A1 | 3/2008 | Matsuo et al. |
| 2008/0097381 A1 | 4/2008 | Moberg et al. |
| 2008/0119705 A1 | 5/2008 | Patel et al. |
| 2008/0172026 A1* | 7/2008 | Blomquist ........ A61M 5/14244 604/500 |
| 2008/0201325 A1* | 8/2008 | Doniger ................... G06N 5/04 |
| 2008/0208627 A1 | 8/2008 | Skyggebjerg |
| 2008/0220752 A1 | 9/2008 | Forstall et al. |
| 2008/0262469 A1* | 10/2008 | Brister ................ A61B 5/0002 604/504 |
| 2008/0287755 A1 | 11/2008 | Sass et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2008/0306434 A1 | 12/2008 | Dobbles et al. |
| 2008/0319383 A1 | 12/2008 | Byland et al. |
| 2009/0054750 A1* | 2/2009 | Jennewine ......... A61B 5/14532 600/316 |
| 2009/0058823 A1 | 3/2009 | Kocienda |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |

(56) References Cited

U.S. PATENT DOCUMENTS

| | | |
|---|---|---|
| 2009/0069787 A1 | 3/2009 | Estes et al. |
| 2009/0089710 A1 | 4/2009 | Wood et al. |
| 2009/0099523 A1 | 4/2009 | Grant et al. |
| 2009/0156990 A1 | 6/2009 | Wenger et al. |
| 2009/0164239 A1* | 6/2009 | Hayter ............... A61M 5/142 |
| | | 705/2 |
| 2009/0197635 A1 | 8/2009 | Kim et al. |
| 2009/0204421 A1 | 8/2009 | Guimaraes |
| 2009/0253970 A1* | 10/2009 | Bashan ............ A61B 5/14532 |
| | | 600/316 |
| 2009/0292247 A1 | 11/2009 | Basso et al. |
| 2010/0016700 A1 | 1/2010 | Sieh et al. |
| 2010/0048358 A1 | 2/2010 | Tchao et al. |
| 2010/0118037 A1 | 5/2010 | Sheikh et al. |
| 2010/0273610 A1 | 10/2010 | Johnson |
| 2010/0280329 A1 | 11/2010 | Randlov et al. |
| 2010/0286601 A1* | 11/2010 | Yodfat ............. A61M 5/14244 |
| | | 604/66 |
| 2010/0298765 A1* | 11/2010 | Budiman ............. A61B 5/4839 |
| | | 604/66 |
| 2010/0305965 A1 | 12/2010 | Benjamin et al. |
| 2010/0315359 A1 | 12/2010 | Seong et al. |
| 2011/0009846 A1 | 1/2011 | Istoc et al. |
| 2011/0040247 A1 | 2/2011 | Mandro et al. |
| 2011/0092788 A1 | 4/2011 | Long et al. |
| 2011/0124996 A1 | 5/2011 | Reinke et al. |
| 2011/0152657 A1* | 6/2011 | Bielawa ........... G01N 33/48792 |
| | | 600/365 |
| 2011/0160555 A1 | 6/2011 | Reifman et al. |
| 2011/0201911 A1 | 8/2011 | Johnson et al. |
| 2011/0238520 A1 | 9/2011 | Selley |
| 2011/0273388 A1 | 11/2011 | Joo et al. |
| 2011/0313349 A1 | 12/2011 | Krulevitch et al. |
| 2011/0319322 A1* | 12/2011 | Bashan ............ A61B 5/14532 |
| | | 514/5.9 |
| 2012/0022496 A1 | 1/2012 | Causey et al. |
| 2012/0053560 A1 | 3/2012 | Kawamura |
| 2012/0150556 A1 | 6/2012 | Galasso et al. |
| 2012/0159328 A1 | 6/2012 | Millington et al. |
| 2012/0215201 A1 | 8/2012 | Brauker et al. |
| 2012/0232520 A1* | 9/2012 | Sloan ............... A61B 5/14532 |
| | | 604/504 |
| 2012/0238999 A1 | 9/2012 | Estes et al. |
| 2012/0330270 A1 | 12/2012 | Colton |
| 2013/0165901 A1* | 6/2013 | Ruchti ................ G16H 20/17 |
| | | 604/504 |
| 2013/0172710 A1 | 7/2013 | Mears et al. |
| 2013/0184547 A1 | 7/2013 | Taub et al. |
| 2013/0245545 A1 | 9/2013 | Arnold et al. |
| 2013/0318439 A1* | 11/2013 | Landis ................ G06F 3/0488 |
| | | 715/705 |
| 2013/0324941 A1 | 12/2013 | Mann et al. |
| 2013/0331659 A1 | 12/2013 | Koski et al. |
| 2013/0338453 A1 | 12/2013 | Duke et al. |
| 2014/0012117 A1* | 1/2014 | Mensinger ............. G16H 40/40 |
| | | 600/365 |
| 2014/0025400 A1 | 1/2014 | Galley et al. |
| 2014/0039383 A1* | 2/2014 | Dobbles ............... G16H 40/63 |
| | | 604/66 |
| 2014/0058749 A1 | 2/2014 | Galley et al. |
| 2014/0068487 A1 | 3/2014 | Steiger et al. |
| 2014/0073892 A1 | 3/2014 | Randloev et al. |
| 2014/0154987 A1 | 6/2014 | Lee et al. |
| 2014/0160078 A1 | 6/2014 | Seo et al. |
| 2014/0309615 A1 | 10/2014 | Mazlish |
| 2014/0317546 A1 | 10/2014 | Jacobson et al. |
| 2014/0344280 A1 | 11/2014 | Wei et al. |
| 2014/0358082 A1 | 12/2014 | Ohzawa |
| 2014/0380218 A1* | 12/2014 | Johnnie ............ A61B 5/150358 |
| | | 715/771 |
| 2015/0025498 A1 | 1/2015 | Estes |
| 2015/0067527 A1* | 3/2015 | Gardner ............... G06F 3/0482 |
| | | 715/739 |
| 2015/0073337 A1 | 3/2015 | Saint et al. |
| 2015/0073754 A1 | 3/2015 | Okkonen et al. |
| 2015/0080842 A1 | 3/2015 | Mathys |
| 2015/0112264 A1 | 4/2015 | Kamen et al. |
| 2015/0141912 A1 | 5/2015 | Estes |
| 2015/0173674 A1 | 6/2015 | Hayes et al. |
| 2015/0277722 A1 | 10/2015 | Masterson et al. |
| 2016/0000998 A1* | 1/2016 | Estes ..................... A61K 38/26 |
| | | 604/892.1 |
| 2016/0038675 A1 | 2/2016 | Estes et al. |
| 2016/0058939 A1 | 3/2016 | Brewer et al. |
| 2016/0072841 A1 | 3/2016 | Caporal et al. |
| 2016/0089491 A1 | 3/2016 | Smith |
| 2016/0110064 A1 | 4/2016 | Shapira |
| 2016/0139671 A1 | 5/2016 | Jun et al. |
| 2016/0228641 A1 | 8/2016 | Gescheit et al. |
| 2016/0235913 A1 | 8/2016 | Smith et al. |
| 2016/0250422 A1 | 9/2016 | Koch et al. |
| 2016/0317743 A1 | 11/2016 | Estes |
| 2016/0357371 A1 | 12/2016 | Lee |
| 2016/0361494 A1 | 12/2016 | J rg et al. |
| 2017/0003848 A1 | 1/2017 | Wakayanagi et al. |
| 2017/0017374 A1 | 1/2017 | Herz |
| 2017/0049957 A1 | 2/2017 | Michaud |
| 2017/0056591 A1* | 3/2017 | Breton ................ A61M 5/1723 |
| 2017/0100538 A1 | 4/2017 | Mhatre et al. |
| 2017/0165416 A1 | 6/2017 | Saint |
| 2017/0173262 A1 | 6/2017 | Veltz |
| 2017/0176952 A1* | 6/2017 | Misaki ................ G04G 9/0076 |
| 2017/0189614 A1 | 7/2017 | Mazlish et al. |
| 2017/0193184 A1 | 7/2017 | Hayter et al. |
| 2017/0199985 A1 | 7/2017 | Mazlish et al. |
| 2017/0203030 A1 | 7/2017 | Brewer et al. |
| 2017/0203036 A1 | 7/2017 | Mazlish et al. |
| 2017/0203037 A1 | 7/2017 | Desborough et al. |
| 2017/0203038 A1 | 7/2017 | Desborough et al. |
| 2017/0203039 A1 | 7/2017 | Desborough et al. |
| 2017/0216524 A1* | 8/2017 | Haider .................. G16H 20/17 |
| 2017/0224910 A1 | 8/2017 | Yodfat et al. |
| 2017/0232195 A1 | 8/2017 | Desborough et al. |
| 2017/0242975 A1 | 8/2017 | Kahlbaugh |
| 2017/0255771 A1* | 9/2017 | Miyakawa .......... G06F 3/04883 |
| 2017/0316592 A1 | 11/2017 | Kamath et al. |
| 2017/0332952 A1 | 11/2017 | Desborough et al. |
| 2017/0348484 A1 | 12/2017 | Duke et al. |
| 2017/0351842 A1* | 12/2017 | Booth ................... G16H 40/63 |
| 2018/0001006 A1 | 1/2018 | Schade et al. |
| 2018/0036495 A1 | 2/2018 | Searle et al. |
| 2018/0089395 A1* | 3/2018 | Desborough ....... A61M 5/3202 |
| 2018/0101297 A1 | 4/2018 | Yang et al. |
| 2018/0133397 A1 | 5/2018 | Estes |
| 2018/0147362 A1 | 5/2018 | Arenas et al. |
| 2018/0150614 A1 | 5/2018 | Sokolovskyy et al. |
| 2018/0161499 A1 | 6/2018 | Al-Ali et al. |
| 2018/0200435 A1 | 7/2018 | Mazlish et al. |
| 2018/0200436 A1 | 7/2018 | Mazlish et al. |
| 2018/0200437 A1 | 7/2018 | Mazlish et al. |
| 2018/0200438 A1 | 7/2018 | Mazlish et al. |
| 2018/0200439 A1 | 7/2018 | Mazlish et al. |
| 2018/0200441 A1 | 7/2018 | Desborough et al. |
| 2018/0207380 A1 | 7/2018 | Lantz et al. |
| 2018/0361060 A9* | 12/2018 | Rosinko ................. A61M 5/142 |
| 2019/0001067 A1 | 1/2019 | Berey et al. |
| 2019/0015024 A1 | 1/2019 | Desborough et al. |
| 2019/0175841 A1 | 6/2019 | Sjolund et al. |
| 2019/0183434 A1 | 6/2019 | Sjolund et al. |
| 2019/0184111 A1 | 6/2019 | Sjolund et al. |
| 2019/0265871 A1 | 8/2019 | Eim et al. |
| 2019/0274624 A1 | 9/2019 | Mazlish et al. |
| 2019/0348166 A1* | 11/2019 | Booth ................... G16H 20/17 |
| 2020/0042166 A1 | 2/2020 | Burns et al. |
| 2020/0097131 A1 | 3/2020 | Bowden et al. |
| 2020/0201494 A1 | 6/2020 | Allington et al. |
| 2020/0236212 A1 | 7/2020 | Vinna et al. |

FOREIGN PATENT DOCUMENTS

| | | |
|---|---|---|
| CN | 102300501 A | 12/2011 |
| CN | 105899247 A | 8/2016 |
| DE | 19627619 | 1/1998 |

(56) References Cited

FOREIGN PATENT DOCUMENTS

| | | |
|---|---|---|
| DE | 10236669 A1 | 2/2004 |
| EM | 0006276170001 | 1/2007 |
| EM | 0006276170002 | 1/2007 |
| EM | 0006276170003 | 1/2007 |
| EM | 0007326490001 | 6/2007 |
| EM | 0007326490002 | 6/2007 |
| EM | 0031267050001 | 7/2016 |
| EM | 0031267050002 | 7/2016 |
| EM | 0031267050003 | 7/2016 |
| EM | 0031267050004 | 7/2016 |
| EP | 0062974 A1 | 10/1982 |
| EP | 0275213 A2 | 7/1988 |
| EP | 0496141 A1 | 7/1992 |
| EP | 0580723 A1 | 2/1994 |
| EP | 0612004 A1 | 8/1994 |
| EP | 0721358 A1 | 7/1996 |
| EP | 1045146 A2 | 10/2000 |
| EP | 1136698 A1 | 9/2001 |
| EP | 1177802 A1 | 2/2002 |
| EP | 1495775 A1 | 1/2005 |
| EP | 1527792 A1 | 5/2005 |
| EP | 1754498 A1 | 2/2007 |
| EP | 1818664 A1 | 8/2007 |
| EP | 2585252 A1 | 5/2013 |
| FR | 2585252 A1 | 1/1987 |
| GB | 0747701 | 4/1956 |
| GB | 2218831 A | 11/1989 |
| WO | 90/15928 A1 | 12/1990 |
| WO | 95/09021 A1 | 4/1995 |
| WO | 97/21457 A1 | 6/1997 |
| WO | 98/04301 A1 | 2/1998 |
| WO | 98/11927 A1 | 3/1998 |
| WO | 98/57683 A1 | 12/1998 |
| WO | 99/21596 A1 | 5/1999 |
| WO | 99/39118 A1 | 8/1999 |
| WO | 99/48546 A1 | 9/1999 |
| WO | 01/72360 A1 | 10/2001 |
| WO | 01/91822 A1 | 12/2001 |
| WO | 01/91833 A1 | 12/2001 |
| WO | 02/40083 A2 | 5/2002 |
| WO | 02/57627 A1 | 7/2002 |
| WO | 02/68015 A2 | 9/2002 |
| WO | 02/84336 A2 | 10/2002 |
| WO | 2002/100469 A2 | 12/2002 |
| WO | 03/26726 A1 | 4/2003 |
| WO | 2003/103763 A1 | 12/2003 |
| WO | 2004/056412 A2 | 7/2004 |
| WO | 2004/110526 A1 | 12/2004 |
| WO | 2005/002652 A2 | 1/2005 |
| WO | 2005/039673 A2 | 5/2005 |
| WO | 2005/072794 A2 | 8/2005 |
| WO | 2005/072795 A2 | 8/2005 |
| WO | 2006/067217 A2 | 6/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |
| WO | 2007/141786 A1 | 12/2007 |
| WO | 2010/091102 A1 | 8/2010 |
| WO | 2011/163450 A1 | 12/2011 |
| WO | 2016/019192 A | 2/2016 |
| WO | 2017/009724 | 1/2017 |

OTHER PUBLICATIONS

Bode et al., Diabetes Management in the New Millennium Using Insulin Pump Therapy, Wiley InterScience 2002, pp. 514-520. (Year: 2002).*

Grill et al., Exercise and Postprandial Lipid Metabolism: an Update on Potential Mechanisms and Interactions with High-Carbohydrate Diets /(Review), Elsevier 2003, pp. 122-132. (Year: 2003).*

Harvey et al., Quest for the Artificial Pancreas, IEEE 2010, pp. 53-62. (Year: 2010).*

Delaney, Chelsey, "4 apps for tracking your fertility" Jun. 6, 2016, Bedsider, site visited Oct. 19, 2018: https://www.bedsider.org/ features/ 647-4-apps-for-tracking-your-fertility.

"Clean Toggle Button Navigation Menu PSD" Jan. 24, 2014, WeLoveSoLo, site visited Oct. 19, 2018: https://www.welovesolo. com/clean-toggle-button-navigation-menu-psd/.

Sara Krugman, Bionic Pancreas User Interface (3/4): Interface Details, Tidepool.org, Jul. 20, 2015.

T:slimx2 Insulin Pump User Guide, Tandem Diabetes Care, Jul. 22, 2016.

Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.

Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.

Guy A. Dumont, Feedback Control for Clinicians, Springer Science+ Media, Apr. 12, 2013, New York.

Fischer et al., In Vivo Comparison of Different Algorithms for the Artificial Beta-Cell, Artificial Organs, 9(2), International Society for Artificial Organs, May 1985, New York.

David A. Copp, Ravi Gondhalekar, and Joao P. Hespanha, Simultaneous Model Predictive Control and Moving Horizon Estimation for Blood Glucose Regulation in Type 1 Diabetes, Optimal Control Applications and Methods, Wiley InterScience, DOI: 10.1002/oca, pp. 1-15, Oct. 2016.

Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.

E. Salzsieder, G. Albrecht, E. Jutzi, and U. Fischer, Estimation of Individually Adapted Control Parameters for an Artificial Beta Cell, Biomedica Biochimica Acta. 43(5) pp. 585-596, May 1984.

Baruah, Insulin Pens: The Modern Delivery Devices, Google Scholar 2011, pp. 38-40. (Year: 2011).

International Search Report for PCT Application No. PCT/US2017/ 53811, dated Dec. 26, 2017, 4 pages.

Written Opinion of the International Searching Authority for PCT Application No. PCT/US2017/053811, dated Dec. 26, 2017, 6 pages.

Synchronise, IOS 7 Interface Symbol. By Flaticon. Freepik.com. Date: 2015. Retrieved from Internet: <https://www.freepik.com/ free-icon/synchronise-ios-7-interface-symbol_751804.htm#term= arrows&page=69&position=14> (Year: 2015).

Refreshing. By Flaticon. Freepik.com. Date: 2016. Retrieved from Internet: <https://www.freepik.com/free-icon/refreshing_807573. htm#term=arrows&page=26&position=26> (Year: 2016).

Refresh Arrow Loop. By Flaticon. Freepik.com. Date:2014. Retrieved from Internet: <https://www.freepik.com/free-icon/refresh-arrow-loop_705291 .htm#term=arrows&page=49&position=43> (Year: 2014).

Kuwayama, Yasaburo. Trademarks & Symbols. vol. 2: Symbolical Designs. Van Nostrand Reinhold Company. Date published: 1973. p. 136. (Year: 1973).

Dreyfuss, Henry. Symbol Sourcebook. Van Nostrand Reinhold Company. Date published: 1984. p. 28. (Year: 1984).

Curved Arrow to the Right. By Flaticon. Freepik.com. Date: 2015. Retrieved from Internet: <https://www.freepik.com/free-icon/curved-arrow-to-the-right_735735.htm#term=arrows&page=59&position= 69> (Year: 2015).

Arrows, Couple, IOS 7 Interface Symbol. By Flaticon. Freepik.com. Date: 2015. Retrieved from Internet: <https://www.freepik.com/ free-icon/arrows-couple-ios-7-interface-symbo_751266.htm#term= arrows&page=68&position=43> (Year: 2015).

Arrows Curves Forming an Oval Shape. By Flaticon. Freepik.com. Date: 2015. Retrieved from Internet: <https://www.freepik.com/ free-icon/arrows-curves-forming-an-oval-shape_746143.htm> (Year: 2015).

Arrow Repeat. By Flaticon. Freepik.com. Date: 2014. Retrieved from Internet: <https://www.freepik.com/free-icon/arrow-repeat_ 694329.htm#term=arrows&page=47&position=67> (Year: 2014).

(56) References Cited

OTHER PUBLICATIONS

Xilas Temp Touch, "The latest in high-tech and convenient devices," DOCNews, vol. 2, No. 7, Jul. 1, 2005, http://docnews.diabetesjournals.ordlcgi/contenl/foll/2/7i 13, 3 pages.

The Medtronic Diabetes Connection, 2006, 6 pages.

Patent Abstracts of Japan, vol. 1999, No. 04, and JP 11 010036, Apr. 30, 1999 and Jan. 19, 1999, Toray Ind. Inc.

OmniPod Quick Start Guide, 2007, 2 pages.

OmniPod Insulin Management System—Investor Relations—Press Release, Feb. 1, 2005, http://investors.insulet.com/phoenix.zhtml?c=209336&p=irol-newsArticle&ID=988708&highlight=1 page.

Medtronic News Release, "Medtronic Receives FDA Approval for World's First Insulin Pump with Real-time Continuous Glucose Monitoring," Apr. 13, 2006, 3 pages.

JDRF, Statistics: JDRF and Diabetes, http://jdrf.org/about-jdrf/fact-sheets/jdrf-anddiabetes- statistics/, 2014.

Hurley, Dan. Artificial Pancreas Makers Race to Market. Discover. Date published: Apr. 12, 2016. <http://discovermagazine.com/2016/may/13-priming-the-pump>.

Debiotech News Release, "Debiotech reveals its new miniaturized Disposable Insulin Nanopump™ for Diabetes therapy," available at http://www.debiotech.com/news/nw 159.html Apr. 24, 2006, 3 pages.

Collins and Lee, "Microfluidic flow transducer based on the measurement of electrical admittance," Lab Chip, 2004,4:7-10.

Centers for Disease Control and Prevention, Number (in Millions) of Adults with Diabetes by Diabetes Medication Status, United States, 1997-2011, http://www.cdc.gov/diabetes/statistics/meduse/fig1.htm, 2013.

Bigfoot Biomedical Reveals its Automated Insulin Delivery System. diaTribe. Date published: Jan. 25, 2016 <https://diatribe.org/bigfoot-biomedical-reveals-its-automated-insulin-delivery-system>.

Bhalla, Raveesh, Understanding Material Design Part II, Sep. 28, 2014, Medium.com [online], [site visited Apr. 11, 2018], Available from Internet: https://medium.com/@raveeshbhalla/understanding-material-design-cf2d60a16de3 (Year: 2014).

Accu-Chek Spirit, "Pump Therapy Made for You," Roche, 2006, 6 pages.

"Omnipod Horizon: Automated Glucose Control" Jun. 2017, 2 pages.

Hoskins, Mike, NEWS: Bigfoot Closed Loop, Jul. 17, 2017, Healthline.com [online], [visited Jan. 22, 2019]. Internet: https://web.archive.org/web/20170810052840/https://www.diabetesdaily.com/blog/bigfoot-biomedical-aims-to-take-multiple-daily-injections-to-the-next-level-with-timesulin-acquisition (Year: 2017).

Smart et al., "Can children with type 1 diabetes and their caregivers estimate the carbohydrate content of meals and snacks?" Diabetic Medicine, 27, No. 3 (2010) pp. 38-353.

Zhang et al., Second Insulin Pump Safety Meeting: Summary Report, Journal of Diabetes Science and Technology 2010, pp. 488-493. (Year: 2010).

Pearson, Practical Aspect of Insulin Pen Devices, Journal of Diabetes Science and Technology 2010, pp. 522-531. (Year: 2010).

Simmons, Cory, "How to Make Your Own Button UI Kit with Super-Clean Syntax" Dec. 23, 2014, envato tuts+, site visited Sep. 19, 2019: https://webdesign.tutsplus.com/tutorials/how-to-make-your-own-button-ui-kit-with-super-clean-syntax-cms-22946.

"Medical Set" iconfinder.com Added Apr. 7, 2017. Accessed Jan. 27, 2020. Available online at URL: https://www.iconfinder.com/iconsets/medical-set-5 (Year: 2017).

Ansyari, Nazurrudin. "Circle Badge Set." iconfinder.com. Added Aug. 15, 2016. Accessed Jan. 27, 2020. Available online at URL: https://www.iconfinder.com/iconsets/circle-badge-set (Year: 2016).

Dreyfus, Henry. Symbol Source Book. New York, McGraw-Hill, 1972. pp. 52, 180, and 184. (Year: 1972).

European Extended Search Report and Opinion for European Application No. 17857362.2, dated Apr. 24, 2020, 9 pages.

"Three icons—Ready, Set and Go" Nov. 29, 2015, depositphotos, site visited Apr. 21, 2020: https://depositphotos.com/91436542/stock-illustration-countdown-ready-set-go-colorful.html (Year: 2015).

Karnes, Chris. "Kids Mental Health App." dribbble.com. Feb. 1, 2020. Accessed May 7, 2020. Available online at URL: https://dribbble.com/shots/9841070-Kids-Mental-Health-App (Year: 2020).

Kumar, Rohit. "Health App." dribbble.com. May 14, 2015. Accessed May 7, 2020. Available online at URL: https://dribbble.com/shots/2062723-Health-App (Year: 2015).

Shishir, Shahidl Islam. "Med-i App | Splash Home and Logo." dribbble.com. Jul. 28, 2019. Accessed May 7, 2020. Available online at URL: https://dribbble.com/shots/6852974-Med-i-App-l-Splash-Home-and-Logo (Year: 2019).

Eren-Oruklu et al., Adaptive Control Strategy for Regulation of Blood Glucose Levels in Patients with Type 1 Diabetes, ScienceDirect2009, pp. 1333-1346. (Year: 2009).

Owens et al., Run-to-Run Control of Blood Glucose Concentrations for People with Type 1 Diabetes Mellitus, IEEE 2006, pp. 996-1005. (Year: 2006).

\* cited by examiner

PERSONALIZING PRESET MEAL SIZES IN INSULIN DELIVERY SYSTEM

CROSS-REFERENCE TO RELATED APPLICATION

A claim for benefit of priority to the Sep. 27, 2016 filing date of the U.S. Patent Provisional Application No. 62/400,366, titled "PERSONALIZING PRESET MEAL SIZES IN INSULIN DELIVERY SYSTEM" (the '366 Provisional Application), is hereby made pursuant to 35 U. S. C. § 119(e). The entire disclosure of the '366 Provisional Application is hereby incorporated herein.

TECHNICAL FIELD

This invention relates to the personalizing of preset meal sizes for a user to enter meal data into an insulin delivery system. For example, one or more meal icons can be personalized to describe an amount or range of amounts of carbohydrates for an insulin bolus calculation.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e., the presence of an excessive amount of analyte, such as glucose, within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Self-monitoring of blood glucose and the self-administration of insulin is the typical method for treating diabetes. In order to assist with this self-treatment, many diabetes-related devices (e.g., blood glucose meters, insulin pumps, etc.) are equipped with insulin bolus calculators that have the user input a number of carbohydrates consumed (or about to be consumed) and the bolus calculator outputs a recommended size for the insulin bolus dosage. Although bolus calculators remove some of the calculations that need to be made by the user in determining an appropriate insulin bolus dosage, bolus calculators still burden the user with the mental task of determining the number of carbohydrates in their meal. Accordingly, there is a need for methods, systems, and devices that further reduce the cognitive burden on the user while improving the accuracy of a recommended insulin bolus dosage.

BRIEF SUMMARY

Some embodiments include an insulin delivery system that includes an insulin delivery device adapted to receive insulin and deliver insulin subcutaneously; a user interface in communication with the insulin delivery device and adapted to send the insulin delivery device bolus insulin instructions, the user interface including multiple user-selectable icons or buttons each representing an amount of carbohydrates; memory to store one or more user-specific dosage parameter; and a processor in communication with the memory and adapted to receive blood glucose data, the processor being adapted to determine the amount of carbohydrates associated with each of the user-selectable icons or buttons based on at least one of the user-specific dosage parameters, the processor further being adapted to update the amount of carbohydrates associated with each of the user-selectable icons or buttons based upon the blood glucose data.

In some embodiments, the user-selectable icons or buttons each represent an amount of carbohydrates in 5 gram or 10 gram increments. In some embodiments, the amount of carbohydrates represented by each of the icons is determined based on an insulin Sensitivity Factor (ISF), a Carb Ratio (CR), a body weight, an age, a total daily basal dose (TDBD), and/or a combination thereof of a person with diabetes (PWD).

In some embodiments, the processor is further configured to determine an insulin delivery amount based on an amount of carbohydrates associated with a selected one of the user selectable icons or buttons and/or the blood glucose data.

In some embodiments, the user-selectable icons or buttons each represent an amount of carbohydrates rounded to the nearest 5 grams.

In some embodiments, the insulin delivery system may include a glucose monitor adapted to monitor the glucose level of a person with diabetes and provide blood glucose data to the processor.

In some embodiments, the amount of carbohydrates associated with each of the user-selectable icons is determined from postprandial blood glucose data.

Some embodiments may include a method that includes displaying at least three icons on a user interface of a mobile device, including a first icon associated with the at least three icons associated with a first carbohydrate level, a second icon associated with the at least three icons associated with a second carbohydrate level, and a third icon associated with the at least three icons associated with a third carbohydrate level; receiving a user selection of one of the three icons through the user interface of the mobile device; determining an insulin bolus level from the user selection; and communicating the insulin bolus level to an insulin delivery device.

In some embodiments, the method may include receiving blood glucose data; wherein the insulin bolus level is determined in part from the blood glucose data.

In some embodiments, adjusting the first carbohydrate level, the second carbohydrate level, and the third carbohydrate level based on an insulin Sensitivity Factor (ISF), a Carb Ratio (CR), a body weight, an age, a total daily basal dose (TDBD) (which can be characterized as a rate), and/or a combination thereof of a person with diabetes (PWD).

In some embodiments, the insulin bolus level is communicated to the insulin delivery device in response to a user selection indicating delivery of the insulin, wherein the user selection includes a fail-safe procedure.

In some embodiments, the insulin bolus level is communicated to the insulin delivery device in response to a user selection indicating delivery of the insulin, wherein the user selection includes a plurality of taps or gestures from a user.

In some embodiments, the first carbohydrate level is rounded to the nearest 5 grams, the second carbohydrate level is rounded to the nearest 5 grams, and the third carbohydrate level is rounded to the nearest 5 grams.

In some embodiments, the method may include receiving postprandial blood glucose data; and adjusting at least one of the first carbohydrate level, the second carbohydrate level, and the third carbohydrate level based on the postprandial blood glucose data.

In some embodiments, the method may include the insulin bolus level is determined from one or more of the following factors the number of carbohydrates divided by the PWD's carbohydrate-to-insulin ratio, a difference between the current blood glucose level and a target blood glucose level divided by the PWD's insulin sensitivity factor, a reading from a blood glucose meter (BGM), data from a continuous glucose monitor (CGM), data from a flash glucose monitor, blood glucose trend data, Insulin on Board (IOB) data, Carbohydrates on Board (COB) data, whether the PWD is or plans to exercise, whether the PWD is sick, whether the PWD is pregnant, whether the PWD is experiencing menses, and/or whether the PWD has consumed certain medications.

BRIEF DESCRIPTION OF THE DRAWINGS

Example embodiments will be described and explained with additional specificity and detail through the use of the accompanying drawings in which.

DETAILED DESCRIPTION

Devices, systems, and methods provided herein are adapted to reduce the cognitive burden on a user seeking to administer insulin for a meal while improving the accuracy of insulin bolus recommendations. In some cases, devices, systems, and methods provided herein can provide a plurality of preset meal sizes represented as icons or buttons for the user to select, which can represent the size of a typical meal for the user, a larger meal for the user, or a small meal for the user (and optionally tiny meals or extra-large meals for the user). In some cases, the number of carbohydrates assigned to each preset icon or button can be personalized for the user based on other user-specific dosage parameters entered by the user for an insulin delivery system (e.g., total daily basal dosage of insulin (e.g., U/day), a total daily dose of insulin, a carbohydrate ratio, an insulin sensitivity factor, a glucose setpoint, or a combination thereof). In some cases, the number of carbohydrates assigned to each preset icon or button can be personalized over time based on estimations of the size of each meal consumed when that icon or button is selected based on a glucose response after the consumption of each meal. In some cases, the number of carbohydrates assigned to each preset icon or button can be rounded to the nearest 5 grams of carbohydrates. In some cases, a user may manually enter personalized meal sizes for a number of user selectable icons or buttons. In some cases, a display can include the number of carbohydrates assigned to each preset icon or button. In some cases, after a user selects an icon, the user can select another user-selectable icon or button to deliver the recommended insulin bolus dose. In some cases, the user can modify the recommended insulin bolus dose prior to administering the bolus dose and select another user-selectable icon or button to deliver the altered insulin bolus dose. In some cases, the user can manually input a number of carbohydrates for a specific meal and modify number of carbohydrates assigned to a user-selectable icon or button. In some cases, a bolus calculation can use blood glucose data (e.g., from a BGM or estimated from a CGM) to adjust the bolus calculation to account for an elevated or low blood glucose level, which can optionally be displayed as a separate calculation separate from the calculation of the part of the bolus that is due to the consumption of carbohydrates. In some cases, methods, systems, and devices provided herein can use glucose data (e.g., from a continuous glucose monitor or flash glucose monitor) to automate the delivery of basal insulin.

Figure 1:
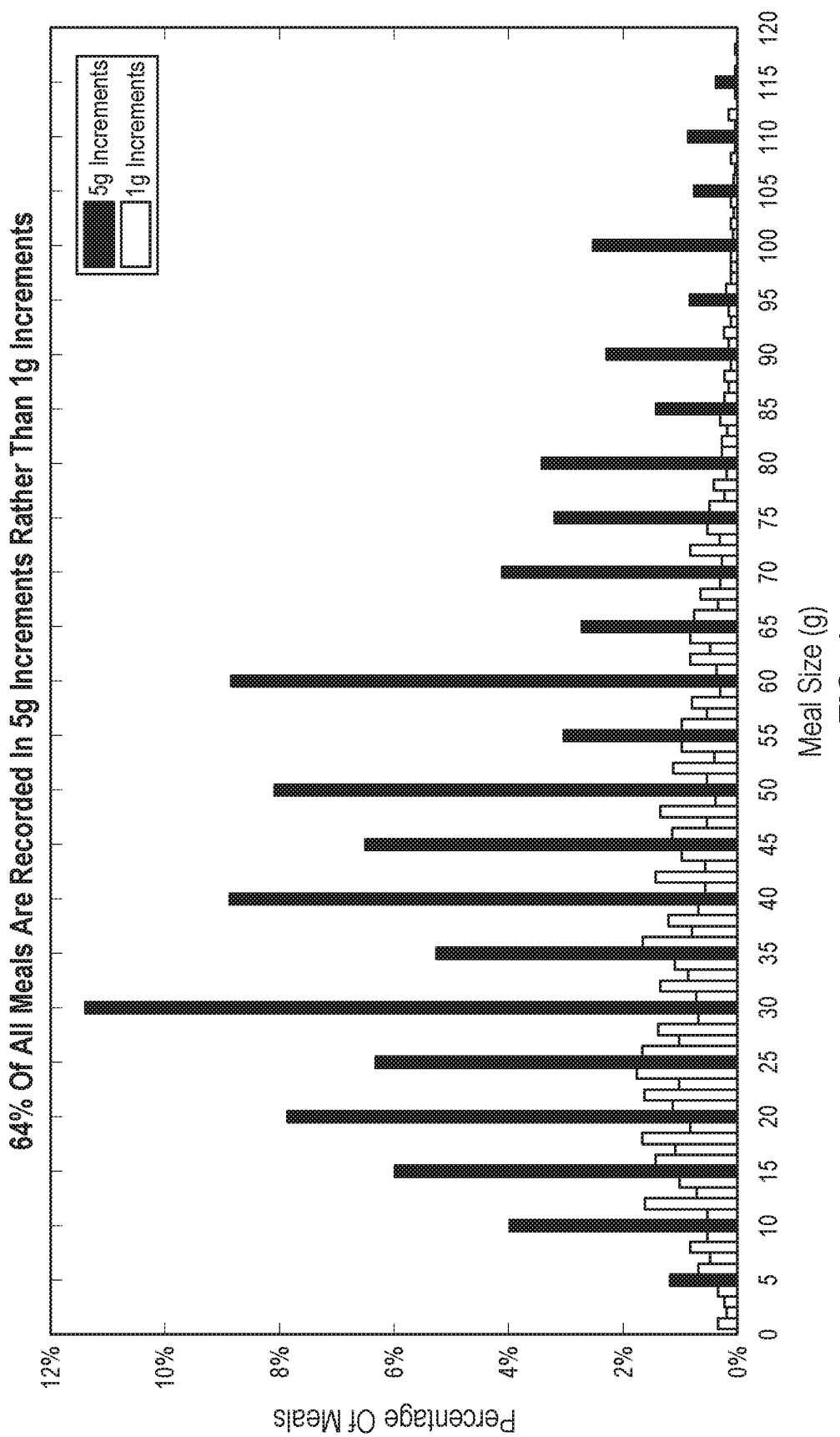
FIG. 1 provides an example graph illustrating recorded meal sizes for boluses.
Figure 2:
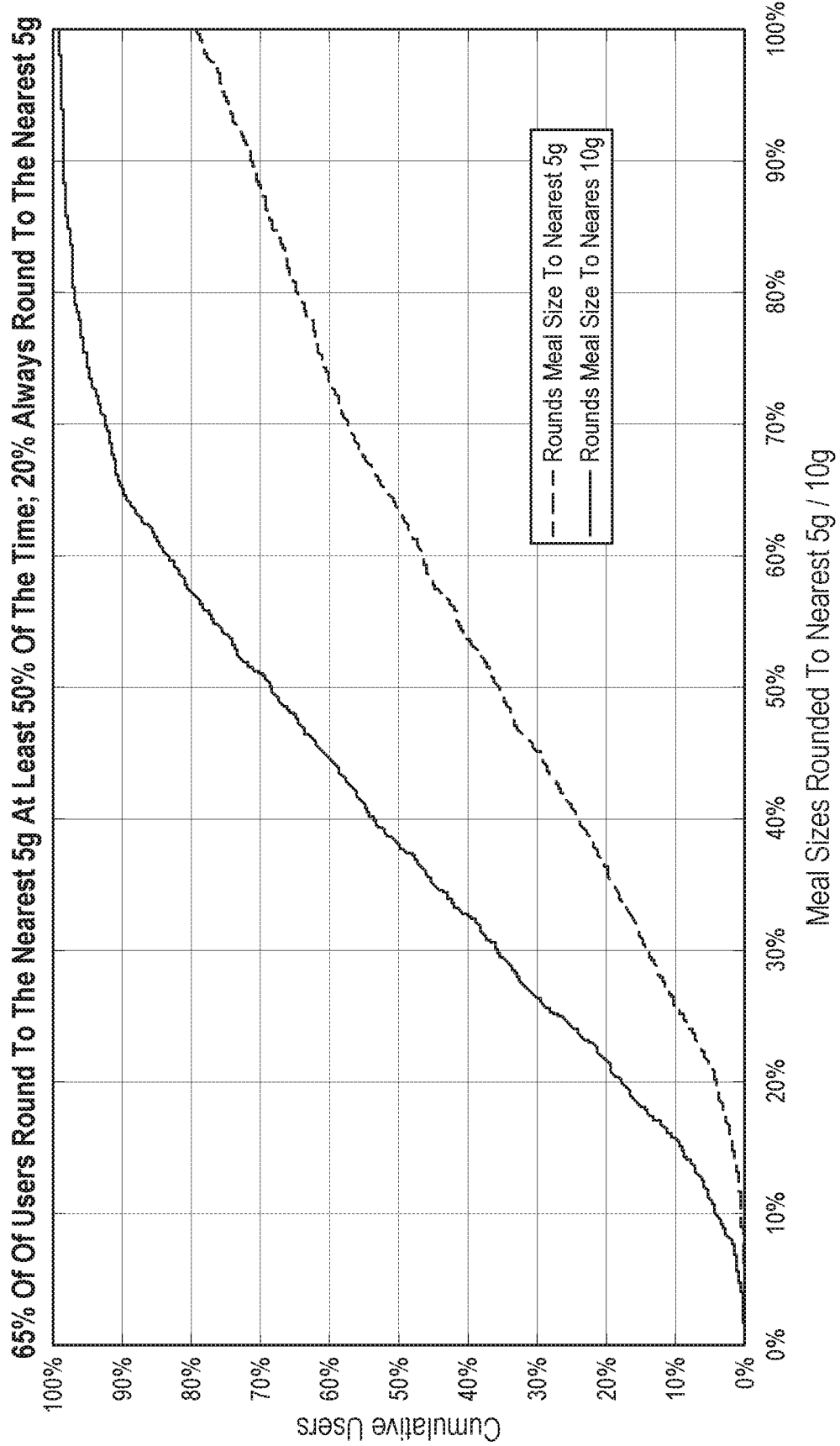
FIG. 2 provides an example graph illustrating percentages of users that rounded meal sizes for boluses.

A review of real user meal inputs from users of an insulin delivery system including a bolus calculator can reveal that users typically enter meal sizes in increments of 5 grams. This bias towards increments of 5 grams reveals that many users of bolus calculators do not feel confident in their ability to accurately calculate their carbohydrate consumption down to 1-gram increments. A study of 969 subjects having 245,397 meal inputs revealed that 64% of those meals were recorded in 5 g increments, as depicted in FIG. 1. This data set also revealed that 65% of users rounded to the nearest 5 g at least 50% of the time and 20% always rounded to the nearest 5 g, as shown in FIG. 2.

Moreover, even if more users felt comfortable in attempting to make more specific estimations of the carbohydrate content of the foods that they select to eat, there is little data to suggest that these users would typically be within 5 grams of the actual carbohydrate count. For example, "*Can children with type* 1 *diabetes and their caregivers estimate the carbohydrate content of meals and snacks?*" C. E. Smart, K. Ross, J. A. Edge, B. R. King, P. McElduff, and C. E. Collins, *Diabetic Medicine,* 27, No. 3 (2010) pp. 38-353 illustrates the range or error there is in children having type 1 diabetes estimating the number of carbohydrates in meals and snacks.

Devices, systems, and methods provided herein can in some cases include user-selectable icons or buttons that describe (or represent) the size of a meal (e.g., in grams) in more subjective terms. In some cases, a user-selectable icon can be labeled as a medium sized meal or as a typical meal. In some cases, a user-selectable icon can be labeled as a small meal, a smaller meal, or a tiny meal. In some cases, a user-selectable icon can be labeled as a large meal, a larger meal, or an extra-large meal. In some cases, a user interface for bolus calculations can include a plurality of user-selectable icons or buttons that are each programmed with an amount of carbohydrates that are personalized for the subjective interpretation for that user. For example, some users might have a typical or medium sized meal of 50 grams while others might have a typical or medium sized meal of 20 grams. Additionally, users might have different subjective interpretations of what is a small meal, a medium meal, and a large meal for that specific user. Accordingly, by personalizing the sizes of meals for that specific user such that it matches the user's subjective understandings, devices, systems, and methods provided herein can achieve better bolus dose recommendations without burdening the user to try to estimate a number of carbohydrates for that particular meal.

The personalizing of one or more meal size user-selectable icons or buttons can be achieved using any suitable method. In some cases, a number of carbohydrates assigned to each user-selectable icon or button can be initially set at a predetermined starting point or can be determined based on entered user information, and then iteratively adjusted upward or downward based upon the glycemic response to that selected meal size and bolus over time.

Initial settings for one or more user-selectable icons or buttons included on a device or in a system provided herein can be preset to predetermined values or ranges (e.g., small=20 g or 15-25 g, medium=30 g or 30-45 g, large=50 g or 50-75 g, and extra-large=80 g or 80-100 g) or can be set based on entered user data or based on one or more user-specific dosage parameters entered into a device or system provided herein. In some cases, initial settings for the one or more user-selectable icons or buttons can be based on an initially entered or determined and programmed total daily basal dose (TDBD)/basal rate (e.g., U/day).

Figure 3:
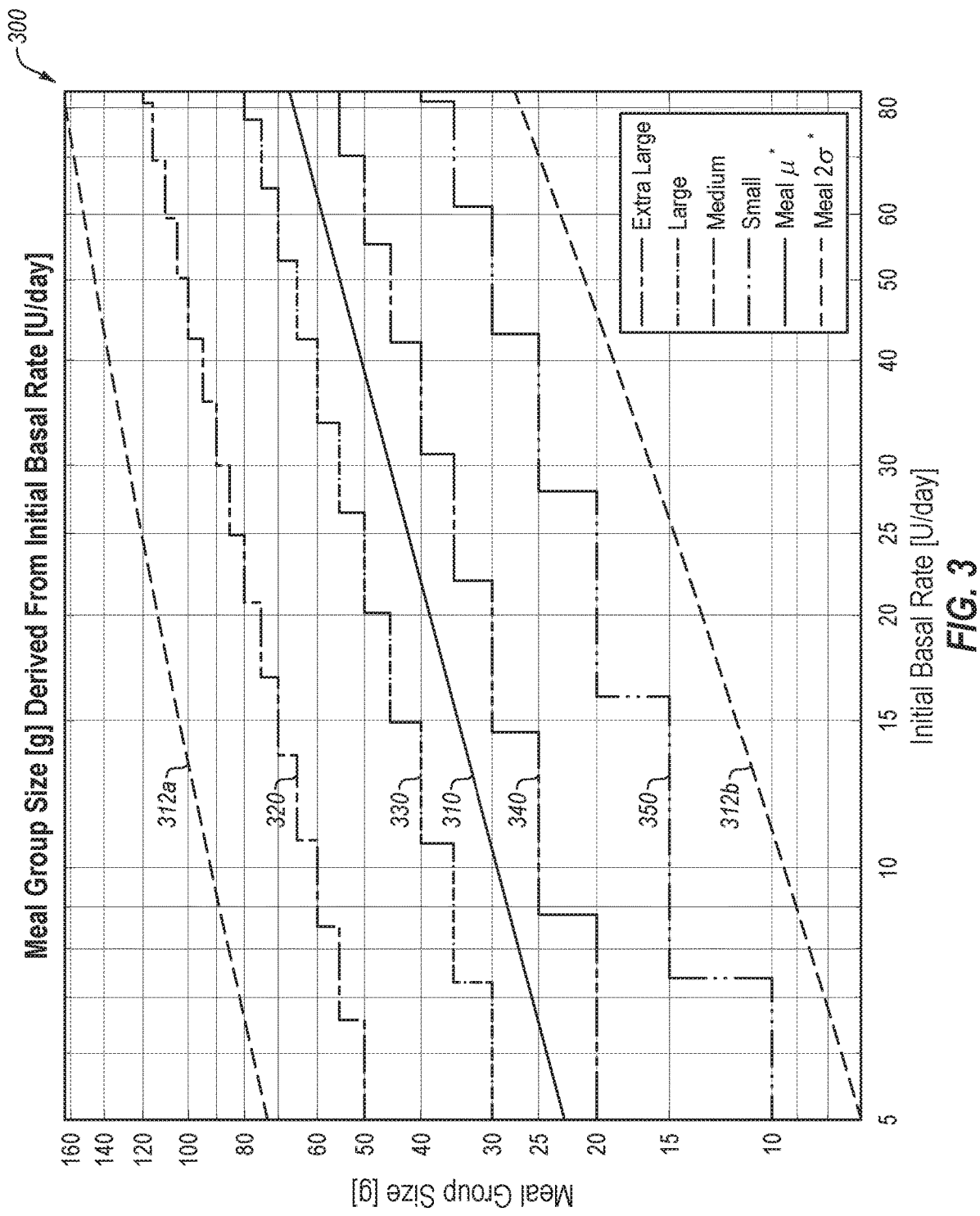
FIG. 3 provides an example graph illustrating a relationship between an initial basal rate and a meal group size.

FIG. 3 depicts a chart 300 illustrating example settings for 4 user-selectable icons or buttons based on an initially entered or determined TDB rate. In some cases, the preset values can be based on the Insulin Sensitivity Factor (ISF), Carb Ratio (CR), body weight, age, TDBD, and/or a combination thereof of the person with diabetes (PWD).

FIG. 3 illustrates the relationship between Basal Rates (BR) in units of [U/day] and Geometric Mean Meal Size $\mu^*_{MS}$ in units of [g] (illustrated as 310 in FIG. 3) as characterized by the line corresponding to the major axis of the hyperellipsoid: $\mu^*_{MS}=12.1 \cdot BR^{0.387}$. The relationship between the Geometric Mean Meal Size and Geometric Standard Deviation Meal Size ($\sigma^*_{MS}$) is: $\sigma^*_{MS}=1.92-\mu^*_{MS}/186$. FIG. 3 includes the Geometric Mean Meal Size as 310 and two times the Geometric Standard Deviation Meal Size as 312a and 312b. Accordingly, FIG. 3 illustrates initial meal size groups as corresponding to the 10% (as a small meal 350), 35% (as a medium meal 340), 65% (as a large meal 330), and 90% percentiles (as an extra-large meal 320) of the Meal Size distribution by combining the above equations and rounding meal size groups to the nearest 5 grams. Thus, by way of example, for a user who had an initial basal rate of 10 U/day, the initial setting for the small meal size button or icon may correspond to 15 g (observed by the intersection of the small meal 350 with the initial basal rate of 10 U/day), the initial setting for the medium meal size button or icon may correspond to 25 g (observed by the intersection of the medium meal 340 with the initial basal rate of 10 U/day), the initial setting for the large meal size button or icon may correspond to 35 g (observed by the intersection of the large meal 330 with the initial basal rate of 10 U/day), and the initial setting for the extra-large meal size button or icon may correspond to 60 g (observed by the intersection of the extra-large meal 320 with the initial basal rate of 10 U/day).

In some cases, the relationship between typical meal sizes and other user-specific dosage parameters can be determined according to population statistics. For example, using the study of 969 subjects and their entered meal sizes discussed above, the distribution of log transformed Basal Rate (BR) in units of [U/day], Carb Ratio (CR) in units of [g/U], Insulin Sensitivity Factor (ISF) in units of [mg/dl/U], and meal size (MS) in units of [g] can be represented using the following multivariable normal, with mean and covariance matrices $\mu$ and $\Sigma$:

$$x \sim N(\mu, \Sigma);$$

$$\mu = \begin{bmatrix} \mu_{ln(BR)} \\ \mu_{ln(CR)} \\ \mu_{ln(ISF)} \\ \mu_{ln(MS)} \end{bmatrix}$$

$$\Sigma = \begin{bmatrix} \sigma^2_{ln(BR)} & \sigma_{ln(BR),ln(CR)} & \sigma_{ln(BR),ln(ISF)} & \sigma_{ln(BR),ln(MR)} \\ \sigma_{ln(BR),ln(CR)} & \sigma^2_{ln(CR)} & \sigma_{ln(CR),ln(ISF)} & \sigma_{ln(CR),ln(MR)} \\ \sigma_{ln(BR),ln(ISF)} & \sigma_{ln(CR),ln(ISF)} & \sigma^2_{ln(ISF)} & \sigma_{ln(MR),ln(ISF)} \\ \sigma_{ln(BR),ln(MR)} & \sigma_{ln(CR),ln(MR)} & \sigma_{ln(MR),ln(ISF)} & \sigma^2_{ln(MS)} \end{bmatrix}$$

The mean and covariance matrices computed using robust statistics, with corresponding $\mu^*$, $\sigma^*$, and correlation matrices $\rho$ are:

$$\mu = \begin{bmatrix} 3.0111 \\ 2.3757 \\ 3.8645 \\ 3.6622 \end{bmatrix}$$

$$\Sigma = \begin{bmatrix} 0.2843 & -0.1657 & -0.2216 & 0.0855 \\ -0.1657 & 0.1978 & 0.1863 & -0.0412 \\ -0.2216 & 0.1863 & 0.2968 & -0.082 \\ 0.0855 & -0.0412 & -0.082 & 0.1532 \end{bmatrix}$$

$$\mu' = \begin{bmatrix} 20.3 \; U/day \\ 10.8 \; g/U \\ 47.7 \; \frac{mg}{dl}/U \\ 38.9 \; g \end{bmatrix}; \sigma' = \begin{bmatrix} 1.70 \\ 1.56 \\ 1.72 \\ 1.48 \end{bmatrix} \rho = \begin{bmatrix} 1 & -0.70 & -0.76 & 0.41 \\ -0.70 & 1 & 0.77 & -0.24 \\ -0.76 & 0.77 & 1 & -0.38 \\ 0.41 & -0.24 & -0.38 & 1 \end{bmatrix}$$

Using these equations and rounding to the nearest 5 grams of carbohydrates, the chart of FIG. 3 can be obtained, which shows the distribution a for meal sizes. It is contemplated, however, that additional population studies can be conducted to create better and/or different correlations between the typical, large, medium, and small meal sizes for a PWD based on their TBD, weight, age, ISF, CR, or a combination thereof.

In some cases, the number of carbohydrates associated with each user-selectable icon or button can be displayed on and/or adjacent to the user-selectable icon or button, which can help a user understand how to use the insulin delivery device or system to avoid deskilling the user. For example, seeing the number of carbohydrates assumed for each meal size helps a user that thinks about meals in terms of carbohydrates to adjust to using buttons to indicate a size of a meal. Additionally, by starting with display numbers rounded to the nearest 5 grams, the user can perceive that precision is not required, thus also reducing the cognitive burden on the user. Additionally, as the system iterates to personalize the amount of carbohydrates for each particular user-selectable icon or button, the system can adjust these numbers by smaller units (e.g., by 1 gram) to demonstrate to the user that the system is adjusting the number of carbohydrates associated with user-selectable icon or button.

Methods, systems, and devices provided herein can update the number of carbohydrates associated with each user-selectable icon or button using any suitable method. In some cases, methods, systems, and devices can use postprandial blood glucose data (e.g., between 1 hour and 3 hours after an announced meal) to evaluate whether the PWD likely consumed significantly more or significantly less carbohydrates than programmed for the user-selectable icon or button (e.g., +/−10%, +/−15%, +/−20%, etc., consumer carbohydrates). In some cases, one or more postprandial blood glucose thresholds can be used to evaluate the match between the amount of carbohydrates consumed and the amount of carbohydrates associated with a selected user-selectable meal icon or button. For example, methods, devices, and systems provided herein can ask a user for a postprandial blood glucose reading from a blood glucose meter. In some cases, methods, devices, and systems provided herein can receive postprandial blood glucose data from a continuous glucose monitor or flash glucose monitor. In some cases, methods, systems, and devices provided herein can use a single postprandial blood glucose data point and compare that to one or more upper thresholds and one or more lower thresholds for that period of time to determine whether the number of carbohydrates associated with that user-selectable meal icon or button should be adjusted upward or downward. For example, if a user selects a typical meal icon indicating a meal of 30 grams of carbohydrates, but the 2-hour postprandial blood glucose reading is above 200 mg/dL, the number of grams associated with that icon or button might be adjusted upward by 2 grams, if it is above 170 mg/dL, it might be adjusted upward by 1 gram, if it is below 130 mg/dL, it might be reduced by 1 gram, and if it is below 100 mg/dL, it might be reduced by 2 grams. Accordingly, over time the meal icons may be adjusted to more closely resemble the user's typical consumption patterns. The particular thresholds can be determined based on the postprandial time, the number of grams associated with the meal icon or button, the CR, ISF, and TDB, and setpoint of the PWD, etc.

In some cases, methods, systems, and devices provided herein can additionally automate insulin delivery using blood glucose data. Methods, systems, and devices provided herein can use any suitable algorithm to automate insulin delivery. In some cases, the blood glucose data can be from a continuous glucose monitor or flash glucose monitor. In some cases, methods, systems, and devices provided herein can deliver basal insulin doses throughout the day that vary based on the recent blood glucose data (e.g., within the last hour), estimations of the amount of active insulin in the PWD's body (e.g., Insulin On Board (IOB)), estimations of the amount of active carbohydrates (e.g., carbohydrates on board), an Insulin Sensitivity Factor (ISF), a Carbohydrate-to-Insulin Ratio (CR), and other user-specific dosage parameters. In some cases, methods, devices, and systems provided herein can be a proportional—integral—derivative (PID) controller. In some cases, methods, devices, and systems provided herein can predict future blood glucose levels for different insulin delivery amounts or schedules and can pick an insulin delivery amount or schedule that minimizes a variation from a set point or that reduces the risk of future blood glucose levels exiting a predetermined range of blood glucose levels. An example of a suitable control algorithm is described in U.S. application Ser. No. 15/601,282, which is incorporated by reference herein in its entirety.

Methods, devices, and systems provided herein can use any suitable insulin delivery device or artificial pancreas system or closed loop insulin delivery system. In some cases, the insulin delivery device can be an insulin pump. In some cases, the insulin delivery device can be an insulin pump having a controller adapted to automate basal insulin delivery based on communications from a CGM or flash glucose monitor, such as described in U.S. application Ser. No. 15/601,282. Additionally or alternatively, the basal insulin delivery may be based on communication from a flash glucose monitor. In some cases, the insulin delivery device can be a smart insulin pen.

Methods, devices, and systems provided herein can in some cases have a user interface on a remote controller device (e.g., a smartphone) as described in U.S. application Ser. No. 15/601,282. In some cases, a remote controller device can wirelessly communicate (e.g., via Bluetooth Low Energy, Near-Field Communications, etc.) with an insulin delivery device (e.g., an insulin pump or a smart insulin pen) to send a request or instruction to the insulin delivery device regarding the information needed to deliver the calculated amount of insulin bolus. In some cases, methods, systems, and devices provided herein can include an insulin pump as the insulin delivery device and allow a user to deliver a bolus without the user directly accessing the insulin pump. In some cases, methods, systems, and devices provided herein can require a user to confirm a bolus delivery on an insulin pump before the bolus is delivered. In some cases, methods, systems, and devices provided herein may send a setting or instruction to a smart insulin pen (with or without allowing the user to alter the setting), but require that the user use the smart insulin pen to actually deliver each bolus.

A user interface on a remote controller device can include the user-selectable meal icons or buttons described above. In some cases, a remote controller device can be a wrist watch. In some cases, methods, devices, and systems provided herein can, in some cases, include a user interface that is part of an insulin delivery device that includes the user-selectable icons or buttons described above. In some cases, the user interface having the user selectable icons or buttons described above can be included on other devices, such as a BGM, a CGM, a flash glucose monitor, an insulin pump, a smart insulin delivery pen, or any other device associated with a PWD.

Figure 4A:
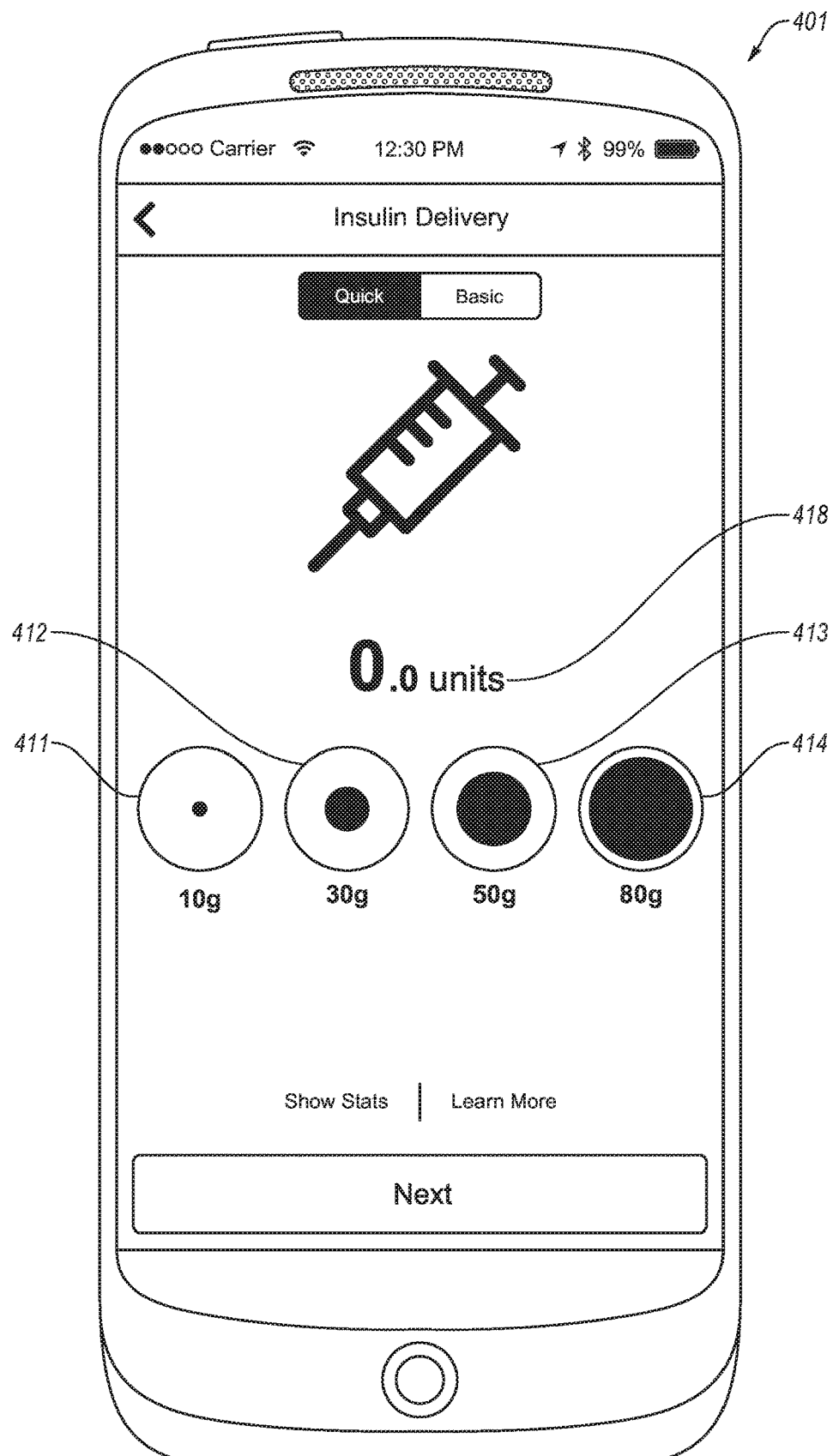
FIG. 4A illustrates an example interface for inputting a bolus.
Figure 4B:
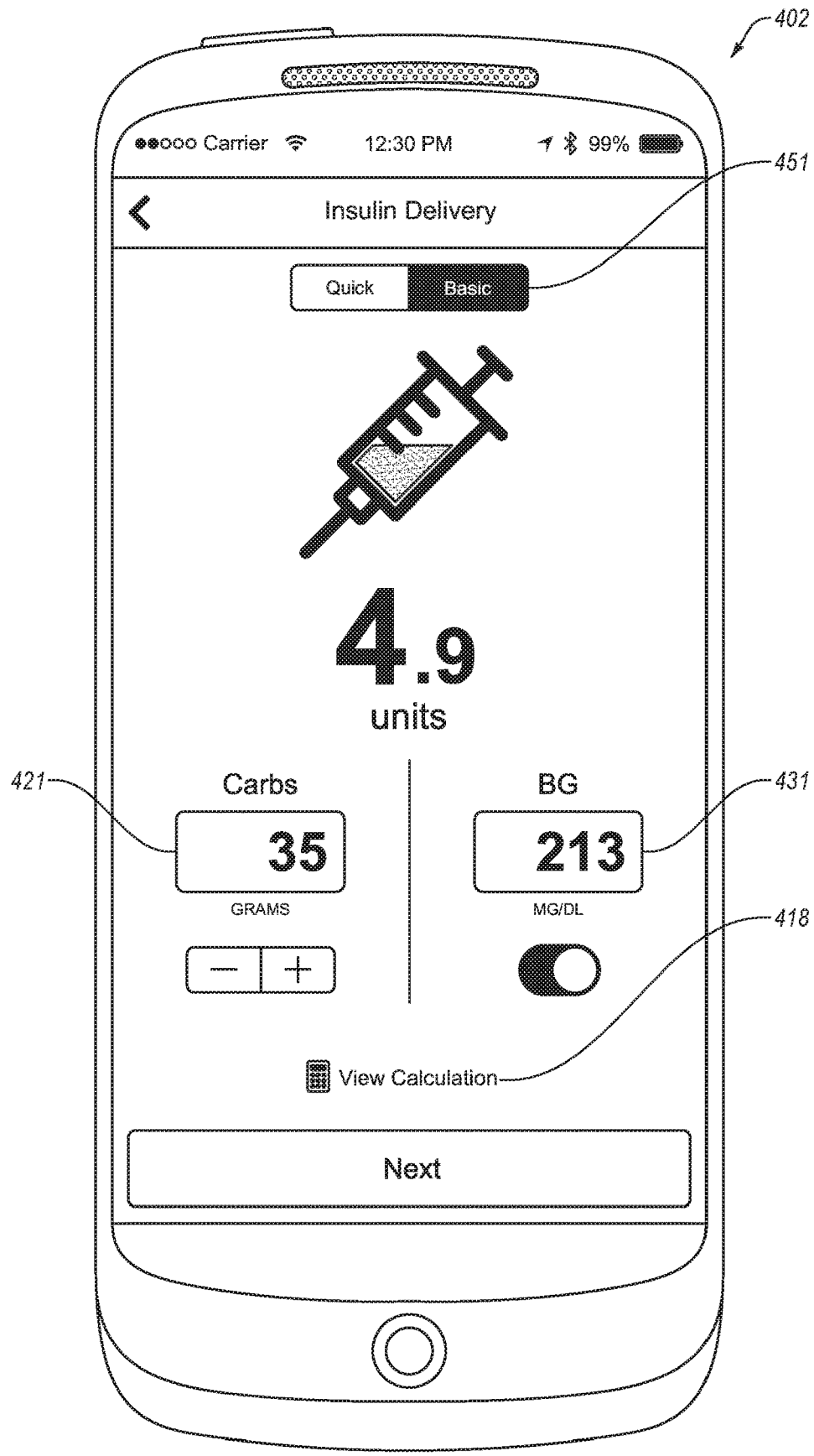
FIG. 4B illustrates another example interface for inputting a bolus.
Figure 4C:
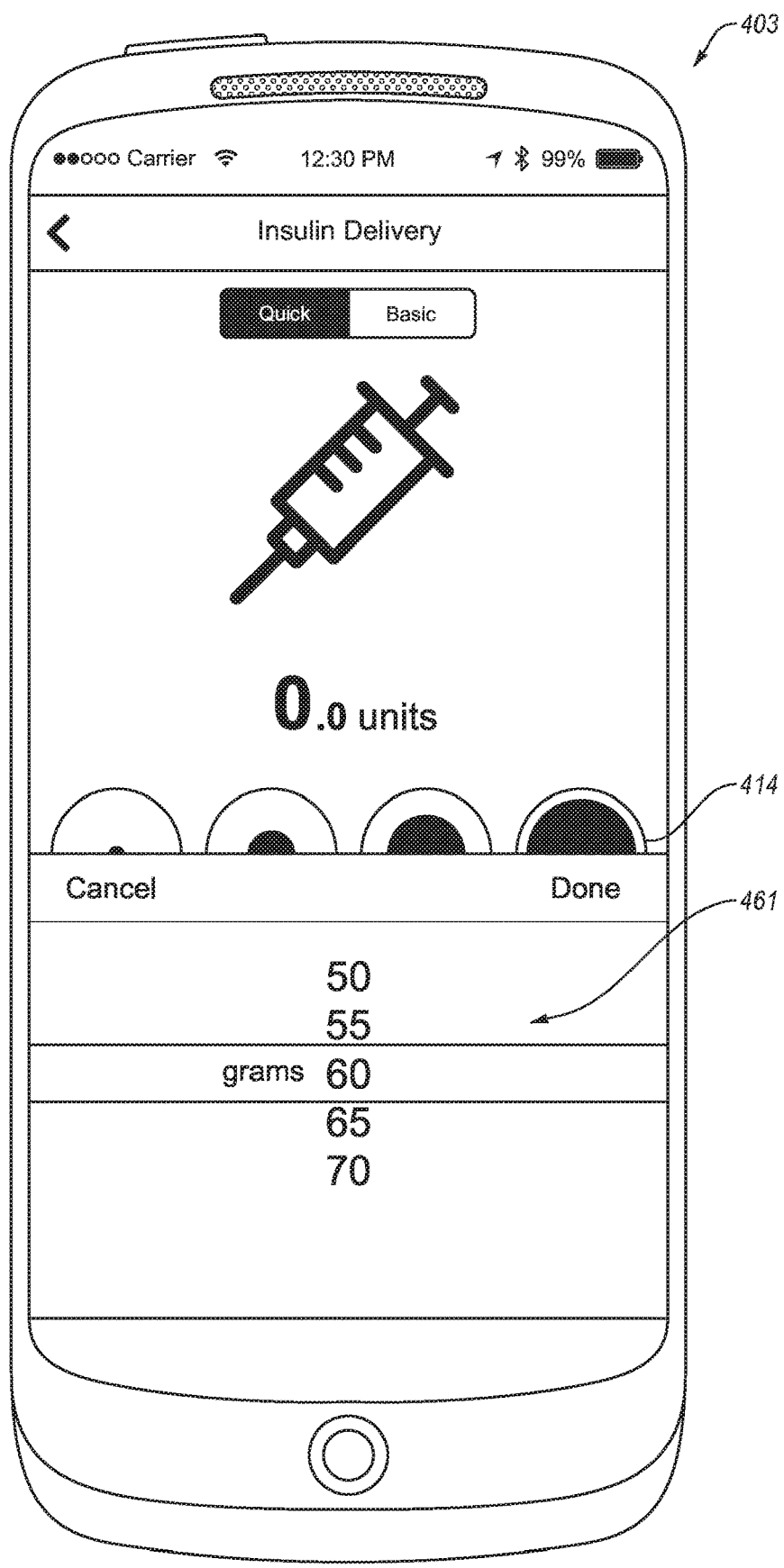
FIG. 4C illustrates another example interface for inputting a bolus.
Figure 4D:
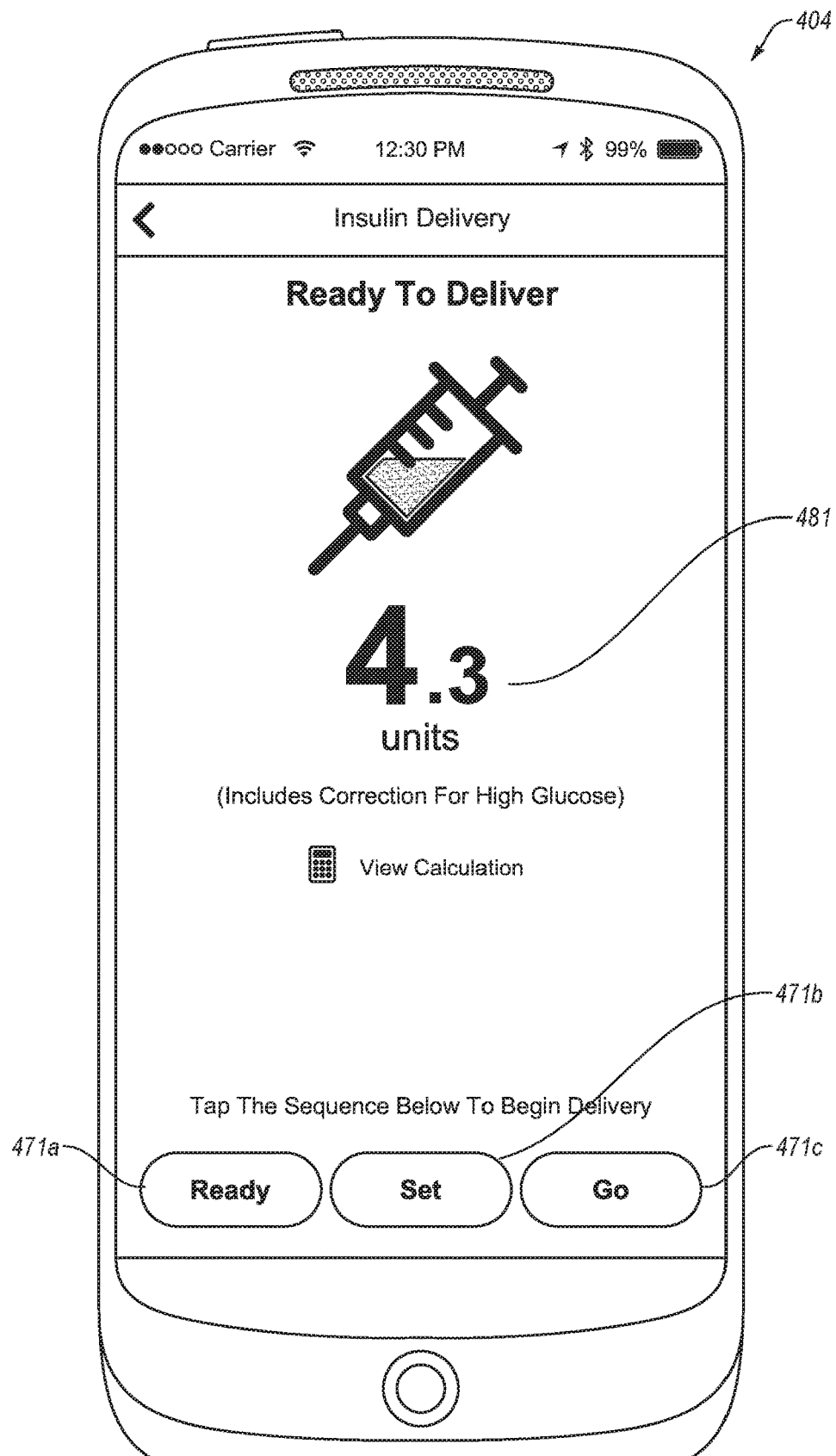
FIG. 4D illustrates an example interface for initiating a bolus.
Figure 4E:
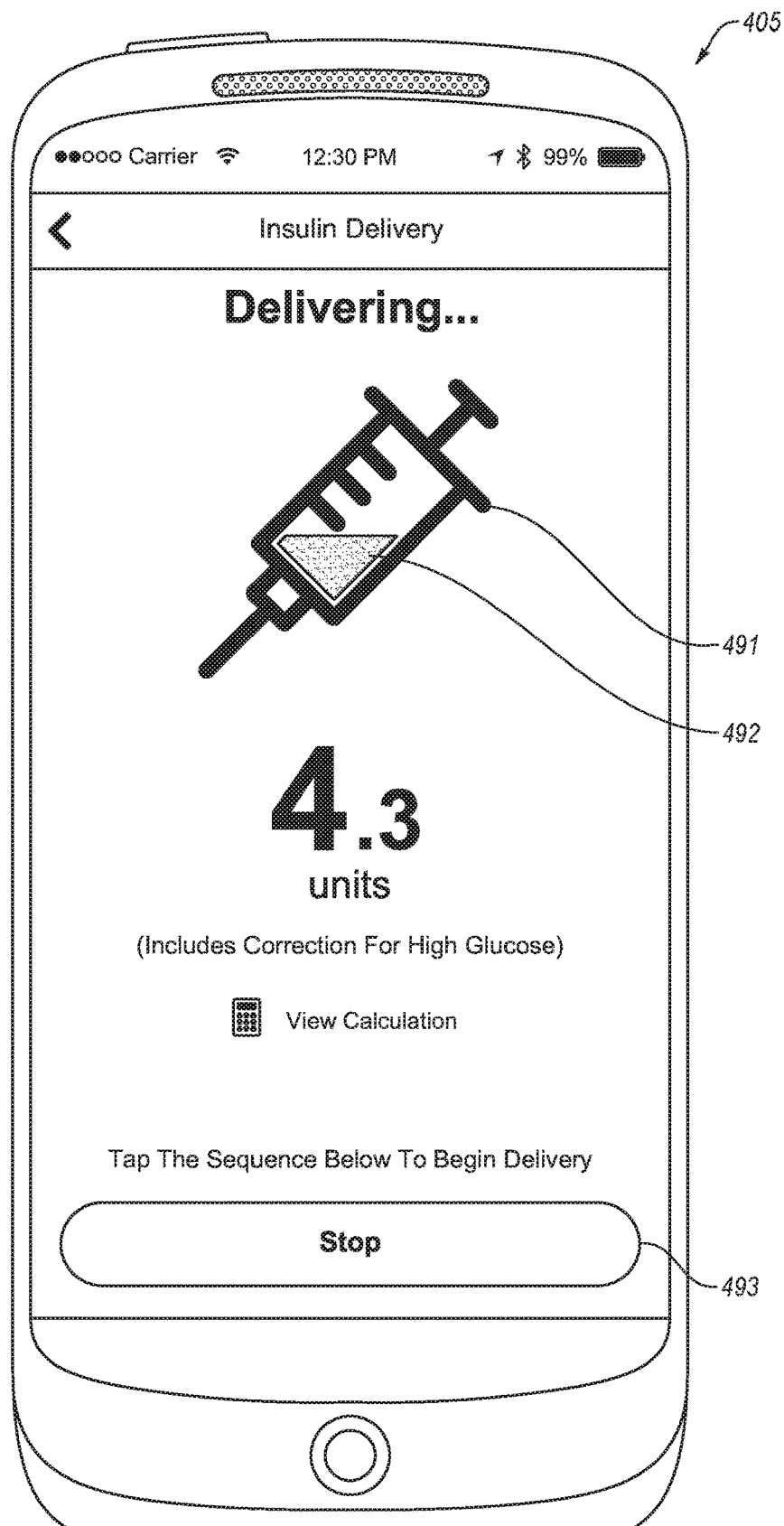
FIG. 4E illustrates an example interface while a bolus is being delivered.

FIGS. 4A through 4E illustrate various example interfaces in accordance with the present disclosure. For example, FIG. 4A illustrates an example interface for inputting a bolus; FIG. 4B illustrates another example interface for inputting a bolus; FIG. 4C illustrates another example interface for inputting a bolus; FIG. 4D illustrates an example interface for initiating a bolus; and FIG. 4E illustrates an example interface while a bolus is being delivered.

As illustrated in FIGS. 4A and 4B, a user can toggle between (e.g., with buttons 451) a user interface 401 (of FIG. 4A) with a quick bolus screen having user selectable icons 411, 412, 413, and 414 that each represent a different number of carbohydrates (e.g., 10 g, 30 g, 50 g, and 80 g), and a user interface 402 (of FIG. 4B) with a basic bolus screen having a first field 421 that allow a user to enter grams of carbohydrates and/or a second field 431 to display or enter a blood glucose level, which may, for example, be received from a BGM, CGM, or flash glucose monitor. As discussed above, when first starting to use methods, systems, and devices described herein with a PWD, the settings of the selectable icons can be based on the user's TDB (e.g., as shown in FIG. 3) or other user-specific dosage parameters. Over time, the number of carbohydrates can be updated based on postprandial blood glucose data being over or under one or more thresholds. Although shown as 10 g, 30 g, 50 g, and 80 g in FIG. 4A, over time these numbers might eventually read, for example, as 8 g, 34 g, 47 g, and 85 g. In some cases, methods, systems, and devices provided herein may adjust adjacent user-selectable icon or button carbohydrate values to ensure a differentiation. For example, if the medium icon or button 412 is personalized up, the large icon or button 413 may also be adjusted upward to maintain a minimum differentiation between the amount of carbohydrates more than the medium button (e.g., at least 5 g, at least 10 g, or at least some other number of grams). In some cases, after selecting one of the icons 411, 412, 413, and/or 414, the user interface 401 may include a field 418 that may display a number of units of insulin to be delivered corresponding to the selected icon.

In some cases, the different number of carbohydrates associated with each of the user selectable icons 411, 412, 413, and/or 414 can be based on user-specific dosage parameters entered for the PWD when they first start the system. In some cases, the different number of carbohydrates associated with each user selectable icon can become personalized over time based on postprandial blood glucose data. In some cases, the different number of carbohydrates associated with each user selectable icon can vary based on the time of day (e.g., meal sizes might become personalized differently if the meal is in the morning vs. in the evening). In this example, each of the user selectable icons may include a graphic (e.g., a fork, a circle, a food item, or any other graphic) that has a size proportional to or related to the relative number of carbohydrates represented by the selectable icon. While four icons (411, 412, 413, and 414) are displayed, any number of icons may be used that represent different carbohydrate values. As discussed above the carbohydrate values represented by the icons may be predetermined and/or adjusted over time based on the user's postprandial blood glucose data. In some cases, an icon corresponding to a correction bolus only can be displayed.

FIG. 4B illustrates the user interface 402 where a user has toggled to a basic bolus screen where the user can enter a number of carbohydrates in the field 421 and optionally enter a blood glucose reading in the field 431. The user interface 402 can display the corresponding amount of insulin to be delivered for the entered number of carbohydrates and blood glucose level. In some cases, CGM data or flash glucose monitor data can be used in place of or in addition to data input in the field 431 corresponding to a blood glucose reading for the calculation of a bolus. In some cases, the user interface can indicate how much of a bolus is due to the consumed carbohydrates and how much is being administered to correct the current blood glucose level. In some cases, a user using user interfaces 401 and/or 402 of FIGS. 4A and 4B will be shown the number of units of insulin to be delivered (optionally explaining the calculation, which may include a correction component due to CGM data or flash glucose monitor data) before the user is allowed to issue the bolus command.

FIG. 4C illustrates another example interface 403 for inputting a bolus. For example, in some cases, a user might want to enter a more specific amount of carbohydrates, thus methods, systems, and devices provided herein can allow the user to enter a specific amount of carbohydrates. For example, as illustrated in FIG. 4C, an adjustable dial 461 may pop up in the user interface 403 in response to a user pressing and holding an icon (e.g., the icon 414) rather than tapping the icon. A feature such as the adjustable dial may provide multiple carbohydrate values in 5-gram increments centered on the carbohydrate value represented by the icon. For example, if the icon represents 60 grams of carbohydrates then the associated pop up dial may include values greater than and less than 60 grams in 5 gram increments. In some cases, the 5-gram increments for each button are bound by the different number of carbohydrates associated with each of the adjacent user selectable icons. In some cases, a consistent selection of a different number of carbohydrates for a meal size can result in the number of carbohydrates associated with that user selectable icon updating to reflect a meal size typically selected by that user when using that icon (e.g., the meal size that is the median meal size, the meal size that is the median meal size, or the meal size that is the mode of meal sizes selected by that user). It may be that some users may select meal sizes in 5-gram increments, but other users may just quickly tap one of the icons (perhaps assuming that it is close enough and that adjustments to basal insulin rates will compensate for any discrepancy between the number of consumed carbohydrates and the number selected). In these and other embodiments, methods, devices, and systems of the present disclosure may provide functionality that services either approach to entering information to receive a bolus of insulin.

As noted above, the user device may calculate an insulin bolus dose corresponding to the selected carbohydrate amount. The insulin bolus dose may include a meal component (e.g., the number of carbohydrates divided by the PWD's carbohydrate-to-insulin ratio) and a correction component (e.g., the delta between the current blood glucose level and a target blood glucose level divided by the PWD's insulin sensitivity factor). In some cases, the calculation of a correction component may require a recent (e.g., within 15 minutes) reading from a blood glucose meter (BGM). In some cases, a correction component may be based on data from a continuous glucose monitor (CGM), a flash glucose monitor, or any other sensor configured to provide blood glucose levels. In some cases, a bolus calculation may consider blood glucose trend data, Insulin on Board (IOB), and/or Carbohydrates on Board (COB). In some cases, the bolus calculation can consider certain physiological conditions for the PWD, such as whether the PWD is or plans to exercise, whether the PWD is sick, whether the PWD is pregnant, whether the PWD is experiencing menses, and/or whether the PWD has consumed certain medications.

FIG. 4D illustrates an example interface 404 for initiating a bolus. For example, the user interface 404 may require the user to tap multiple buttons 471 (e.g., the buttons 471a, 471b, and/or 471) prior to delivery of insulin. The tapping of multiple buttons in a certain pattern may mitigate against unintentional deliveries of insulin. In this example, the user interface displays icons with the words: "ready," "set," and "go." The second icon may be unselectable until the first icon has been selected. The third icon may be unselectable until the second icon has been selected. Once the three icons have been selected an insulin bolus dose may be delivered to the user, for example, via an insulin delivery pump. Once the three icons have been selected, the application executing on the user device may send a message to an insulin delivery pump, for example, via a wireless communication device (such as an antenna), and/or chipset (such as a Bluetooth device (e.g., Bluetooth Low Energy, Classic Bluetooth, etc.), a Near-field communication (NFC) device, an 802.6 device (e.g., Metropolitan Area Network (MAN), a Zigbee device, etc.), a WiFi device, a WiMax device, cellular communication facilities, etc.), and/or the like, that includes the amount of insulin to be delivered to the user. The requirement to tap multiple buttons may reduce the chances that insulin is inadvertently delivered to the user. The interface 404 may also include a field 481 that displays the number of units of insulin to be delivered in the bolus. Additionally or alternatively, the interface 404 may indicate whether or not the bolus includes a correction portion of the bolus and/or what portion of the bolus is for correction purposes (e.g., to address a high blood glucose level).

In some cases, the order of the buttons 471 may be rearranged each time the user delivers or a bolus, or on any other regular interval. For example, the first time a PWD delivers a bolus in the day the buttons 471 may be in the order from left to right of 471a (Ready), 471b (Set), 471c

(Go); a second time in the day delivering a bolus, the buttons 471 may be in the order from left to right of 471c (Go), 471b (Set), 471a (Ready), etc.

FIG. 4E illustrates an example interface 405 while a bolus is being delivered. In some cases, the interface 405 may include an indicator of the progression of delivery of insulin. For example, the insulin delivery screen may include an icon 491 that illustrates a syringe, with a decreasing amount of fluid 492. Additionally or alternatively, the indicator may include a decreasing numerical percentage, a colored circle that is filling/emptying or being drawn/erased, or any other display or visual indicator of progress of delivering insulin.

In some cases, the interface 405 may include a button or icon 493 that can be selected to stop the delivery of insulin. In some cases, invoking the button or icon 493 may trigger an alert or an alarm to the user that they interrupted the delivery of insulin and inquire whether or not they would like to resume or complete the delivery of the bolus of insulin.

In some cases, a completion screen may be displayed after an insulin bolus has been delivered. Additionally or alternatively, a screen may be displayed that illustrates an alert or an alarm that a blood glucose level is high and a correction bolus may be advisable for the user.

In some cases, a user may invoke an app icon displayed on a home screen of a user device such as, for example, a smart phone. The user can select the app icon via a touch screen or another user interface device, which results in execution of the corresponding application. In some cases, once executed on the user device, the application may include a home screen or landing screen. The home screen may display various data such as, for example, the user's current blood glucose data as received from a BGM, CGM, or flash glucose monitor. Various other data may be presented on the home screen, such as a calculated IOB, a blood glucose trend, and/or previous insulin delivery amounts and/or times. The home screen may also include a selectable button (or icon) that be tapped to allow the user to enter data regarding a meal bolus using a bolus screen. The invocation of such a meal bolus button or icon may lead the user to any of the screens of FIGS. 4A, 4B, 4C, etc.

The user interface described above can be used in an automated insulin delivery system adapted for use by a person having type 1 diabetes, but some aspects of this user interface can used by a person having Type 2 diabetes or gestational diabetes. In some cases, at least some aspects of the bolus user interface described above can be used in in a mobile application to personalize the treatment of Type 2 diabetes.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "approximately" or "about" are to be understood to be given their broadest meaning consistent with the understanding of those skilled in the art. Additionally, the term approximately includes anything within 10%, or 5%, or within manufacturing or typical tolerances.

All examples and conditional language recited herein are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

What is claimed is:

1. An insulin delivery system comprising:
    an insulin delivery device to receive insulin and deliver insulin subcutaneously;
    a user interface in communication with the insulin delivery device to send the insulin delivery device bolus insulin instructions, the user interface comprising a plurality of user-selectable icons or buttons each representing a respective meal size and a respective amount of carbohydrates;
    a memory to store one or more user-specific dosage parameters and data, the data comprising respective amounts of carbohydrates associated with each of the user-selectable icons or buttons; and a processor in communication with the memory to:
associate an amount of carbohydrates with each of the plurality of user-selectable icons or buttons based at least partially on the one or more user-specific dosage parameters, each of the plurality of user-selectable icons or buttons being associated with a different amount of carbohydrates;
receive a selection of a user-selectable icon or button of the plurality of user-selectable icons or buttons;
determine a first insulin delivery amount based at least partially on the amount of carbohydrates associated with the selected user selectable icon or button;
deliver insulin according to the first insulin delivery amount;
receive blood glucose data from a blood glucose monitor and for postprandial periods of time after the delivery of the first insulin delivery amount;
based at least partially on the received blood glucose data, determine that the amount of carbohydrates associated with the selected user selectable icon or button requires adjustment;
based on determining that the amount of carbohydrates associated with the selected user selectable icon or button requires adjustment, automatically, without any user intervention, update the amount of carbohydrates associated with the selected user selectable icon or button based at least partially upon the received blood glucose data;
determine a second insulin delivery amount based at least partially on the updated amount of carbohydrates associated with the selected user selectable icon or button; and
deliver insulin according to the second insulin delivery amount.

2. The insulin delivery system according to claim 1, wherein the plurality of user-selectable icons or buttons each represent an amount of carbohydrates in 5 gram or 10 gram increments.

3. The insulin delivery system according to claim 1, wherein a respective amount of carbohydrates represented by each of the plurality of user-selectable icons or buttons is determined based at least partially on the one or more user-specific dosage parameters comprising an insulin Sensitivity Factor (ISF), a Carb Ratio (CR), a body weight, an age and a total daily basal (TDB) rate of a person with diabetes (PWD).

4. The insulin delivery system according to claim 1, wherein the processor is configured to determine an insulin delivery amount based at least partially on the blood glucose data.

5. The insulin delivery system according to claim 1, wherein each of the plurality of user-selectable icons or buttons represents an amount of carbohydrates rounded to the nearest 5 grams.

6. The insulin delivery system according to claim 1, comprising a glucose monitor to monitor the glucose level of a person with diabetes and provide blood glucose data to the processor.

7. The insulin delivery system according to claim 1, wherein a respective amount of carbohydrates associated with each of the plurality of user-selectable icons or buttons is determined at least partially based on postprandial blood glucose data.

8. A method comprising:
receiving one or more user-specific dosage parameters for a person with diabetes (PWD), wherein the one or more user-specific dosage parameters are selected from the group consisting of an insulin Sensitivity Factor (ISF), a Carb Ratio (CR), a body weight, an age, and a total daily basal (TDB) rate;
determining a first carbohydrate level, a second carbohydrate level, and a third carbohydrate level based at least partially on one or more user-specific dosage parameters;
displaying at least three icons on a user interface of a mobile device, a first icon of the at least three icons associated with the first carbohydrate level and a first meal size, a second icon of the at least three icons associated with the second carbohydrate level and a second meal size, and a third icon of the at least three icons associated with the third carbohydrate level and a third meal size;
receiving a user selection of an icon of the at least three icons through the user interface of the mobile device;
determining a first insulin bolus level based at least partially on a carbohydrate level associated with the selected icon;
communicating the first insulin bolus level to an insulin delivery device;
receiving postprandial blood glucose data from a blood glucose monitor and for postprandial periods of time after the delivery of insulin according to the determined first insulin bolus level;
based at least partially on the received postprandial blood glucose data, determining that the carbohydrate level associated with the selected icon of the at least three icons requires adjustment;
based on determining that the carbohydrate level associated with the selected icon of the at least three icons requires adjustment, automatically, without any user intervention, adjusting at least the carbohydrate level associated with the selected icon of the at least three icons based at least partially on the received postprandial blood glucose data;
determining a second insulin bolus level based at least partially on the adjusted carbohydrate level associated with the selected icon; and
communicating the second insulin bolus level to an insulin delivery device.

9. The method according to claim 8, wherein the insulin bolus level is communicated to the insulin delivery device in response to a user selection indicating delivery of the insulin, wherein the user selection includes a fail-safe procedure.

10. The method according to claim 8, wherein an insulin bolus level is communicated to the insulin delivery device in response to a user selection indicating delivery of the insulin, wherein the user selection includes a plurality of taps or gestures from a user.

11. The method according to claim 8, wherein the first carbohydrate level is rounded to the nearest 5 grams, the second carbohydrate level is rounded to the nearest 5 grams, and the third carbohydrate level is rounded to the nearest 5 grams.

12. The method according to claim 8, wherein an insulin bolus level is determined from factors selected from a list consisting of the number of carbohydrates divided by the PWD's carbohydrate-to-insulin ratio, a difference between the current blood glucose level and a target blood glucose level divided by the PWD's insulin sensitivity factor, a reading from a blood glucose meter (BGM), data from a continuous glucose monitor (CGM), data from a flash glucose monitor, blood glucose trend data, Insulin on Board (IOB) data, Carbohydrates on Board (COB) data, whether the PWD is or plans to exercise, whether the PWD is sick, whether the PWD is pregnant and whether the PWD is experiencing menses, or whether the PWD has consumed certain medications.

13. One or more non-transitory, computer-readable media containing instructions that, in response to being executed by one or more processors, cause a mobile device to perform operations comprising:
- displaying at least three icons on a user interface of the mobile device, a first icon of the at least three icons associated with a first carbohydrate level and a first meal size, a second icon of the at least three icons associated with a second carbohydrate level and a second meal size, and a third icon of the at least three icons associated with a third carbohydrate level and a third meal size;
- receiving a user selection of an icon of the at least three icons through the user interface of the mobile device;
- determining a first insulin bolus level based at least partially on a carbohydrate level associated with the selected icon;
- communicating the first insulin bolus level to an insulin delivery device;
- receiving postprandial blood glucose data from a blood glucose monitor and for postprandial periods of time after the communication of insulin according to the determined first insulin bolus level;
- based at least partially on the received first postprandial blood glucose data, determining that at least one of the first carbohydrate level, the second carbohydrate level, or the third carbohydrate level requires adjustment;
- based on determining that at least one of the first carbohydrate level, the second carbohydrate level, or the third carbohydrate level requires adjustment, automatically, without any user intervention, updating at least one of the first carbohydrate level, the second carbohydrate level, or the third carbohydrate level based at least partially on the first blood glucose data received by the mobile device;
- determining a second insulin bolus level based at least partially on the adjusted carbohydrate level associated with the selected icon; and
- communicating the second insulin bolus level to an insulin delivery device.

14. The computer-readable media of claim 13, wherein an insulin bolus level is communicated to the insulin delivery device in response to a user selection indicating delivery of the insulin, wherein the user selection includes a fail-safe procedure.

15. The computer-readable media of claim 13, wherein an insulin bolus level is communicated to the insulin delivery device in response to a user selection indicating delivery of the insulin, wherein the user selection includes a plurality of taps or gestures from a user.

16. The computer-readable media of claim 13, wherein the first carbohydrate level is rounded to the nearest 5 grams, the second carbohydrate level is rounded to the nearest 5 grams, and the third carbohydrate level is rounded to the nearest 5 grams.

* * * * *

UNITED STATES PATENT AND TRADEMARK OFFICE
CERTIFICATE OF CORRECTION

PATENT NO. : 11,229,751 B2  
APPLICATION NO. : 15/717845  
DATED : January 25, 2022  
INVENTOR(S) : Lane Desborough et al.

Page 1 of 1

It is certified that error appears in the above-identified patent and that said Letters Patent is hereby corrected as shown below:

In the Specification  
Column 6, Line 34, change "distribution a for" to --distribution $\sigma$ for--  
Column 10, Line 36, change "and/or 471" to --and/or 471$c$--

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*